(12) United States Patent
Trau et al.

(10) Patent No.: US 10,156,546 B2
(45) Date of Patent: Dec. 18, 2018

(54) DEVICE AND METHOD FOR THE DETECTION OF TARGET ENTITIES

(71) Applicant: THE UNIVERSITY OF QUEENSLAND, St. Lucia, Queensland (AU)

(72) Inventors: Matt Trau, Balmoral (AU); Muhammad Johirul Alam Shiddiky, Fitzgibbon (AU); Sakandar Rauf, Thuwal (SA); Ramanathan Pudhukode Vaidyanathan, Toowong (AU)

(73) Assignee: THE UNIVERSITY OF QUEENSLAND, Queensland (AU)

( * ) Notice: Subject to any disclaimer, the term of this patent is extended or adjusted under 35 U.S.C. 154(b) by 238 days.

(21) Appl. No.: 14/768,986

(22) PCT Filed: Feb. 19, 2014

(86) PCT No.: PCT/AU2014/000141
§ 371 (c)(1),
(2) Date: Aug. 19, 2015

(87) PCT Pub. No.: WO2014/127409
PCT Pub. Date: Aug. 28, 2014

(65) Prior Publication Data
US 2016/0003771 A1    Jan. 7, 2016

(30) Foreign Application Priority Data

Feb. 19, 2013   (AU) ............................... 2013900529

(51) Int. Cl.
*G01N 27/447*    (2006.01)
*G01N 27/327*    (2006.01)
(Continued)

(52) U.S. Cl.
CPC ........ *G01N 27/447* (2013.01); *B01L 3/50273* (2013.01); *F04B 19/006* (2013.01);
(Continued)

(58) Field of Classification Search
CPC .......... C07K 1/24; C07K 1/26; C12C 1/6813; C12C 2523/31; G01N 27/44791;
(Continued)

(56) References Cited

U.S. PATENT DOCUMENTS 5,632,876 A    5/1997   Zanzucchi et al. .......... 436/6.12

FOREIGN PATENT DOCUMENTS

| EP | 1 391 241 | 2/2004 |
| EP | 1 391 241 A1 | 2/2004 |
| WO | 2007/077498 A1 | 7/2007 |

OTHER PUBLICATIONS

Liu et al., "Development of an AC electrokinetics-based immunoassay system for on-site serodiagnosis of infectious diseases," Sensors and Actuators A 171 (2011) 406-413.*
(Continued)

*Primary Examiner* — Alexander S Noguerola
(74) *Attorney, Agent, or Firm* — Nixon & Vanderhye P.C.

(57) ABSTRACT

A device for the detection of target entities, the device including: a fluidic channel to conduct a liquid sample containing at least one type of target entity to be detected; and mutually spaced electrodes disposed along the fluidic channel; wherein the mutually spaced electrodes are functionalized to selectively bond to the at least one type of target entity and are configured to electro-hydrodynamically pump the liquid sample along the fluidic channel on application of a signal to the electrodes, such that selectivity of attachment of the at least one type of target entity to the electrodes is determined by at least one parameter of the signal.

9 Claims, 36 Drawing Sheets

(51) Int. Cl.
    *B01L 3/00*         (2006.01)
    *F04B 19/00*       (2006.01)
    *G01N 33/483*     (2006.01)
    *C07K 1/26*         (2006.01)

(52) U.S. Cl.
    CPC ..... *G01N 27/3276* (2013.01); *G01N 33/4836* (2013.01); *B01L 2300/0645* (2013.01); *B01L 2400/0415* (2013.01); *C07K 1/26* (2013.01); *C12Q 2565/125* (2013.01); *G01N 27/44791* (2013.01)

(58) Field of Classification Search
    CPC ........... G01N 27/44752; G01N 27/453; G01N 27/44704; C12Q 1/6813; C12Q 2523/31; C12Q 2565/125
    See application file for complete search history.

(56) References Cited

OTHER PUBLICATIONS

Sigurdson et al., "Electrothermal stirring for heterogeneous immunoassays," Lab Chip, 2005, 5, 1366-1373.*
Velev et al., "On-chip micromanipulation and assembly of colloidal particles by electric fields", Soft Matter, vol. 2, 2006, pp. 738-750.
Examination Report No. 1 for Standard Patent Application dated Oct. 13, 2017, issued in Australian Patent Application No. 2014218503.
Didar, Tohid Fatanat, et al., "Adhesion based detection, sorting and enrichment of cells in microfluidic Lab-on-Chip devices," Lab Chip, 2010, vol. 10, pp. 3043-3053.
Extended European Search Report dated Oct. 12, 2016, issued in European Patent Application No. 14754759.0.

* cited by examiner

Asymmetric planar electrodes

Asymmetric electrode pairs with increasing electrode sizes $U_{\mu D2, pair2} > U_{\mu D2, pair1}$ Without ac-EHD With ac-EHD

Bare electrode +ac-EHD

Biotin-modified electrode +ac-EHD

DEVICE AND METHOD FOR THE DETECTION OF TARGET ENTITIES

This application is the U.S. national phase of International Application No. PCT/AU2014/000141 filed 19 Feb. 2014, which designated the U.S. and claims priority to AU Patent Application No. 2013900529 filed 19 Feb. 2013, the entire contents of each of which are hereby incorporated by reference.

TECHNICAL FIELD

The present invention relates to a device and method for the detection of target entities, which may be biological molecules or cells, for example circulating tumor cells, DNA, RNA, and protein bio markers.

BACKGROUND

The progression of cancer in patients is characterized by the invasion of cells between organs through the bloodstream to set up colonies in the different parts of the body. Detecting these 'circulating tumor cells' (also referred to as "CTCs") is extremely challenging owing to their low abundance (e.g., as low as a few cells per mL) in the presence of large numbers of non-target cells and molecules. In recent years, many different forms of microfluidic device have been developed to capture and detect rare CTCs. However, despite their impressive clinical demonstrations, these devices are generally limited in their capabilities.

It is desired to provide a device and method for the detection of target entities that alleviate one or more difficulties of the prior art, or that at least provide a useful alternative.

SUMMARY

In accordance with some embodiments of the present invention, there is provided a device for the detection of target entities, the device including:
  a fluidic channel to conduct a liquid sample containing at least one type of target entity to be detected; and
  mutually spaced electrodes disposed along the fluidic channel;
  wherein the mutually spaced electrodes are functionalised to selectively bond to the at least one type of target entity and are configured to electro-hydrodynamically pump the liquid sample along the fluidic channel on application of a signal to the electrodes, such that selectivity of attachment of the at least one type of target entity to the electrodes is determined by at least one parameter of the signal.

The signal applied to the electrodes can be a DC signal, and the selectivity is determined by the voltage of the signal. Alternatively, the signal applied to the electrodes can be an AC signal, and the selectivity is determined by the amplitude and frequency of the signal. The selectivity may have a maximum as a function of the frequency of the AC signal applied to the electrodes.

In some embodiments, the mutually spaced electrodes are arranged in mutually spaced pairs of said electrodes, the electrodes of each said pair being mutually spaced and of different spatial dimensions so as to electro-hydrodynamically pump the liquid sample when the signal is applied across the electrodes.

In some embodiments, the spacing between the pairs of said electrodes is constant. In some embodiments, the spacing between the pairs of said electrodes changes with distance along the fluidic channel.

In some embodiments, at least one of the electrodes of each pair has a non-planar surface. In some embodiments, the non-planar surface is micromachined or otherwise textured to increase the surface area of the corresponding electrode and to improve mixing of the liquid sample. In some embodiments, the non-planar surface includes features projecting into the fluidic channel. In some embodiments, the features are generally conical.

In some embodiments, the at least one type of target entity includes at least one type of biological entity. In some embodiments, the at least one type of biological entity includes at least one type of cell, DNA, RNA, and/or protein biomarker. In some embodiments, the at least one type of biological entity includes at least one type of circulating tumor cell. In some embodiments, the efficiency of capture of the at least one type of target entity is dependent upon the voltage and/or amplitude of the signal applied to the electrodes.

In accordance with some embodiments of the present invention, there is provided a method for the detection of target entities, the method including:
  introducing a liquid sample containing at least one type of target entity to be detected into a fluidic channel;
  wherein mutually spaced electrodes are disposed along the fluidic channel and are functionalised to selectively bond to the at least one type of target entity, the mutually spaced electrodes being configured to electro-hydrodynamically pump the liquid sample along the fluidic channel on application of a signal to the electrodes, such that a selectivity of attachment of the at least, one type of target entity to the electrodes is determined by one or more parameters of the signal applied to the electrodes;
  selecting at least one of the one or more parameters of the signal to provide enhanced selectivity of the at least one type of target entity; and
  applying a signal having the selected one or more parameters to the electrodes to pump the liquid sample along the fluidic channel, and to selectively bond the at least one type of target entity to the functionalised electrodes.

In some embodiments, the signal applied to the electrodes is a DC signal, the selectivity is determined by the voltage of the signal, and the step of selecting at least one of the one or more parameters includes selecting a voltage of the DC signal to provide enhanced selectivity of the at least one type of target entity.

In some embodiments, the signal applied to the electrodes is an AC signal, and the selectivity is determined by the amplitude and frequency of the AC signal.

In some embodiments, the selectivity has a maximum as a function of the frequency of the AC signal applied to the electrodes, and the step of selecting at least one of the one or more parameters includes selecting a frequency of the AC, signal to provide enhanced selectivity of the at least one type of target entity.

In some embodiments, the method includes selecting at least one parameter of the AC signal other than frequency to further enhance the selectivity of the at least one type of target entity. In some embodiments, the method includes selecting at least one parameter of the AC signal to selectively remove a selected entity from the electrodes. In some embodiments, the method includes controlling at least one parameter of the AC signal to correspondingly control shear forces near the electrodes.

In some embodiments, the at least one type of biological entity includes at least one type of cell, DNA, RNA, and/or protein biomarker.

In some embodiments, the at least one type of target entity includes at least one type of biological entity. In some embodiments, the at least one type of biological entity includes at least one type of circulating tumor cell.

In some embodiments, the selected at least one parameter of the signal increases the efficiency of capture of the at least one type of target entity.

BRIEF DESCRIPTION OF THE DRAWINGS

Some embodiments of the present invention are hereinafter described, by way of example only, with reference to the accompanying drawings, wherein:

FIGS. 14c and 14d are for the EHD-μD3 device.

DETAILED DESCRIPTION

Figure 1:
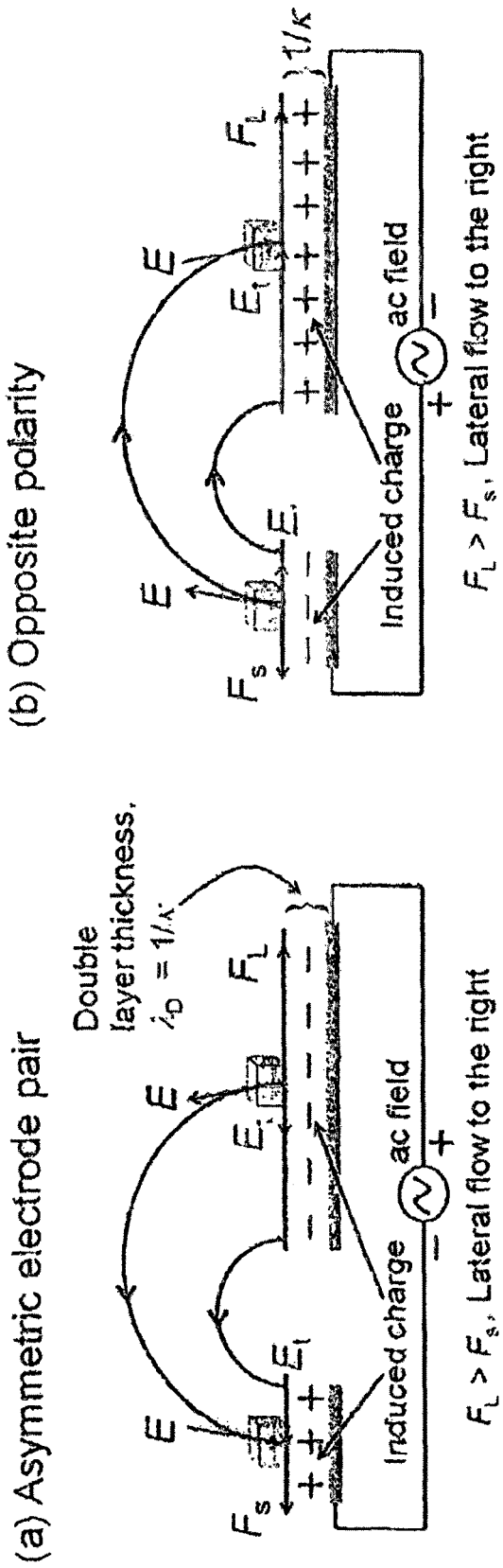
FIG. 1 is a schematic diagram illustrating the mechanism of flow in embodiments of the present invention. An AC electric field E is applied between each pair of electrodes, resulting in induced charges in the double layer. The characteristic thickness of the double layer is given by the Debye length, $\lambda_D$ (=1/κ), which is approximately 2 nm in the described embodiments (as determined by the Debye-Hückel approximation). Upon the application of E, the induced charges in the double layer of each electrode experience a force F (F=ρE, where ρ=charge density) due to interaction with the tangential component of the applied electric field (E), and produce a fluid flow in the direction of the broken symmetry. The asymmetric geometry of the electrodes give rise to a lateral variation in the total amount of free (double layer) charges and spatial distribution of charges on the electrode surface. Consequently the free charges on the larger electrode create stronger lateral forces than those on the smaller electrode ($F_L > F_s$, where $F_L$ and $F_s$ are the resultant forces on larger and smaller electrodes, respectively), resulting in a lateral flow towards the large electrode. Reversing the polarity of the AC field also reverses the sign of the charges in the induced double layer, and since electrical body forces are the product of the charges and the applied field, a steady flow can be maintained towards the large electrode.

Embodiments of the present invention include devices and methods for the detection of target entities that enable the selectivity of capture or attachment (and thus detection) of at least one target entity (e.g., a type of biological cell, biological molecule, analyte, or other molecular species) in a liquid sample to be selectively enhanced. This enhancement results from the ability to selectively control or at least modify the attachment of entities (including entitles other than the at least one targeted entity) to functionalised electrodes in one or more fluidic channels by corresponding control of an electrical signal applied to those electrodes. This is used to simultaneously electrohydrodynamically pump the liquid sample through the fluidic channels by applying generated forces onto charged molecules in and near the double layer at nanometer distances from the electrode surface. The signal may be a direct current (DC) signal or an alternating current (AC) signal.

Although embodiments of the present invention are described herein in the context of detecting biological cells as the targeted entities, it will be apparent to those skilled in the art that the described methods and devices can alternatively be used to detect or otherwise capture essentially any type of entity dispersed in a liquid, providing that that it can be selectively targeted by appropriate functionalising of the electrodes (e.g., with a corresponding specific or complementary capture probe). Accordingly, other embodiments of the invention can be applied to the detection or capture of not only biological cells, but also or alternatively other biological entities (e.g., DNA, RNA, proteins), and/or non-biological entities (e.g., particles, colloids, molecules, etc). Many other suitable types of entities will be apparent to those skilled in the art in light of this disclosure.

It is believed that this selective enhancement results from the fact that the fluid is driven by forces applied at nanometer distances from the electrode surface where the attachment and capture of entities also occurs (including the target entities and other, unwanted entities), and the corresponding ability to control or at least correspondingly modify or determine highly localised electrohydrodynamic shear forces that are induced by the applied DC or AC signal within the double layer ($\lambda_D$=double layer thickness) formed on the surface of the electrodes forms along the surface of the electrodes. Thus a given applied signal gives rise to shear force(s) of corresponding strength(s) that are able to selectively detach (and/or inhibit attachment of) substantially only those entities (e.g., biological cells or molecules) that are (or would be) relatively weakly bonded to the electrodes, leaving substantially only those entities that ere more strongly attached. Consequently, by appropriate selection (or 'tuning') of the parameters of the applied signal, for example, in the case of an AC signal, its frequency, signal amplitude, and signal shape/form (e.g., sinusoidal), or in the case of a DC signal, its amplitude (i.e., DC voltage), it is possible to effectively select the strength of the localised shear forces at the surfaces of the electrodes to selectively remove substantially only those entities that are more weakly attached to the electrodes than a desired target entity (e.g., cell or molecule type). That is, the parameter(s) of the applied signal can be selected or 'tuned' to effectively optimise the selectivity of a selected target biological cell or molecule type, for example.

A significant feature of this ac-EHD induced flow is that all of the free charges in solution occur only within the double layer of the electrode, and thus all of the ac-EHD body forces on the fluid also occur strictly within this region. The electrical double layers are typically on the order of 1-2 nm in size, meaning that the fluid flow is driven by forces within molecular distances of the electrode surface. For this reason, the described methods of selectively displacing non-specific (relatively weakly bound) cells or molecules by selecting or timing fluid shear forces at the nanoscale is referred to as "nanoshearing".

In some embodiments, this method is applied in microfluidic devices that use the electrodes and an applied AC signal to electrohydrodynamically pump liquid samples containing at least one type of target circulating tumor cell (CTC) through microfluidic channels. However, it will be apparent to those skilled in the art that the method can be applied to the detection of essentially any type of cell, molecule, or other type of entity, and to fluidic channels of essentially any dimensions, including nanoscale lateral dimensions.

The electrohydrodynamic ("EHD") devices described herein are also found to enhance mixing of the fluid in the channel(s) in addition to enabling control of the shear forces on the surface of the electrodes modified with specific immunocapture agents. This tunable control of micromixing and the surface shear forces enables two improvements to traditional immunocapture of cells or molecules: (i) enhanced capture efficiencies of target cells or molecules, presumably due to an increased number of sensor-target collisions (as a result of improved cell transport), and (ii) enhanced specificity resulting from the ability to tune microscale and/or nanoscale fluid shear forces at the solid/liquid interface.

The shear forces can be controlled to be sufficiently low to increase attachment of cells to antibody-modified electrodes, since stronger shear forces can wash cells out from the channel and thus limit the cell-surface interactions; conversely, lower shear forces are unable to shear off loosely bound nonspecific cells and molecules.

The phenomenon of EHD induced fluid flow per se is known, but details of the underlying mechanisms are not entirely clear. However, it is believed that one of these mechanisms can be explained as follows. The EHD electrodes are configured in pairs, where the electrodes of each pair have different dimensions such that one of the electrodes has a larger surface area than the other. For this reason, each pair of electrodes is described as being 'asymmetric'.

As shown in FIG. 1, the application of a potential difference between the two electrodes of each pair results in an electric field E that gives rise to opposing forces $F_L$ and $F_S$ on the inducted charges within the double layer of the two electrodes. Due to greater number and higher density of charges on the larger electrode L, the total force $F_L$ on those charges is always greater than the opposing total force $F_S$ on the charges on the smaller electrode S. Additionally, because a change in polarity of the electrical signal applied across a pair of the electrodes reverses not only the electric field direction, but also the polarity of the charges in each double layer, the net force ($F_L-F_S$) always results in a unidirectional fluid flow towards the large electrode, irrespective of the instantaneous polarities of the two electrodes. Thus the fluid is driven in the same direction, irrespective of the polarity of the signal, and consequently whether the applied signal is an AC signal or a DC signal.

In the described embodiments, a series of asymmetric electrode pairs with functionalised surfaces are disposed along a serpentine microfluidic channel. In some embodiments, each pair of electrodes is nominally identical to each other pair, whereas in other embodiments, there are two or more different types of electrode pairs. These differences can include, for example, differences in scale, shape, and/or configuration. In some embodiments, the surface of at least one of the electrodes of each pair has a non-planar, micromachined or otherwise textured surface. The benefits of a non-planar electrode surface includes increasing the effective surface area available for attachment, and modification of the fluid flow pattern to increase mixing and/or the probability of attachment. In some embodiments, the non-planar surface includes micromachined features projecting into the fluidic channel, of which the generally conical or 'spike'-like features described herein are but one example. Many other possible configurations will be apparent to those skilled in the art in light of this disclosure.

EXAMPLES

Example I

To demonstrate the effectiveness of the EHD devices and methods described above, three different types of EHD microfluidic device were fabricated. Each device includes asymmetric micro-scale electrode pairs within an elongate microfluidic channel. A characteristic feature of these devices is the spacing or gap between the short and large electrodes in each electrode pair. The distance between adjacent electrode pairs, the length of each electrode, and the channel dimensions (width (w), height (h) and length (l)) are other important parameters. Unless otherwise stated, all of the devices were made using photolithographic masks designed using the standard photolithographic mask design software application known as "Layout Editor" or L-Edit (V15, Tanner Research Inc., CA).

Figure 2:
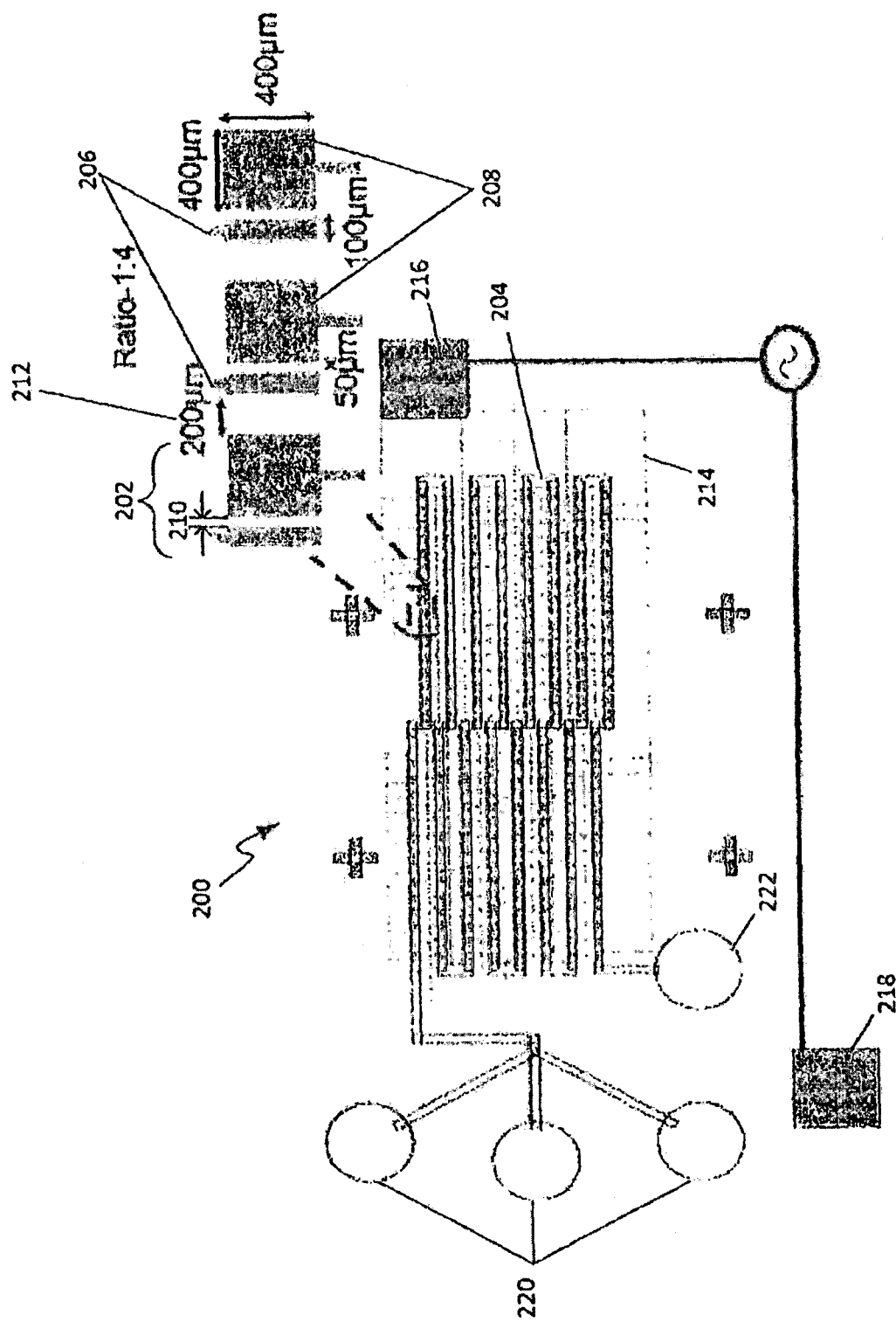
FIGS. 2 to 7|Design of EHD-μD devices. Schematic of layout editor design and corresponding SEM images of enlarged segments in each device of EHD-μD1 (FIGS. 2 and 3), EHD-μD2 (FIGS. 4 and 5), and EHD-μD3 (FIGS. 6 and 7). Microfluidic channels for all three devices were designed with three branching inlets and one single outlet reservoirs.
Figure 3:
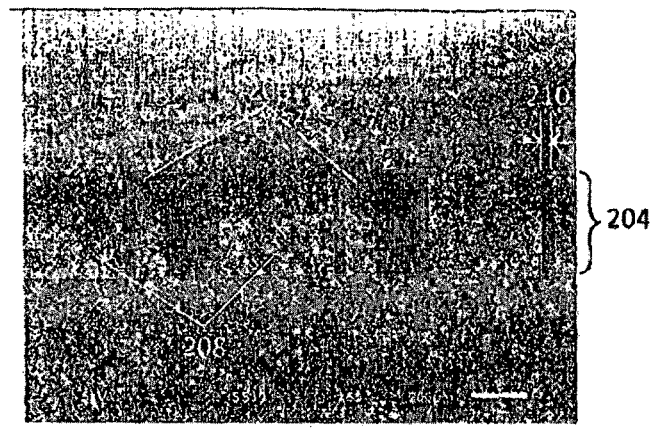

The first device type 200, identified herein as "EHD-µD1" includes an array of nominally identical asymmetric electrode pairs 202 along the base of a long serpentine microfluidic channel 204 of width 400 µm, as shown in FIGS. 2) and 3. Each of these devices contains 256 asymmetric planar electrode pairs 202, each pair 202 including a 'short' electrode 206 of length 100 µm and a 'long' electrode 208 of length 400 µm, mutually separated by a distance or gap 210 of 50 µm, all dimensions being given along the channel length direction.

The electrode pairs are printed on a long serpentine microchannel (w=400 µm; l=196 mm; h=300 µm), as shown in FIG. 2, capped with a polymer coating (SU8-2150 photoresist, in this example) defined by photolithography. In the described embodiment, the serpentine channel is configured as 16 elongate and mutually parallel interconnected 'segments', each segment including 16 electrode pairs arranged along its base. The channel segments are interconnected by relatively short joining channel portions orthogonal to the elongate channel segments to provide a single serpentine fluidic channel. The adjacent electrode pairs in each segment are separated by a distance 212 of 200 µm. The characteristic features of this device are: $r_0/d_2=0.125$, $r_1/d_2=0.5$, $d_1/d_2=0.25$, where $d_2$ and $d_1$ are the lengths of electrodes in each pair 202, $r_0$ is the distance between the electrodes in the pair, and $r_1$ is the distance between adjacent electrode pairs. Each device also includes conducting paths 214 to connect the short electrodes to a first contact pad 216 and the long electrodes to a second contact pad 218. Thus an electrical (AC or DC) signal applied across the first contact pad 216 and the second contact pad 218 is therefore applied across the short electrode 206 and the long electrode 208 of each pair of electrodes in the device 200. Inlet 220 and outlet 222 reservoirs 220 are provided at corresponding ends of the channel 204.

Figure 5:
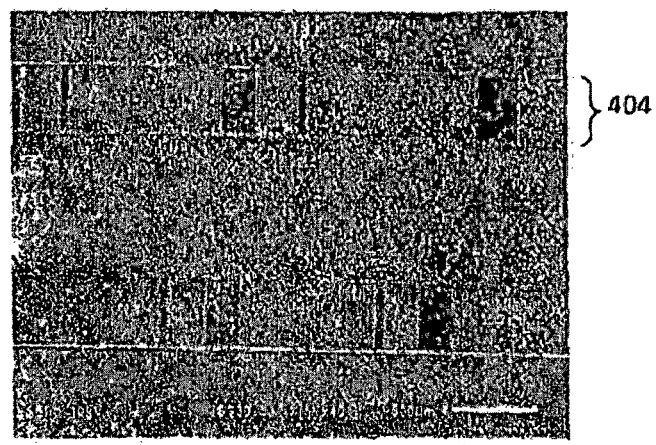
Figure 4:
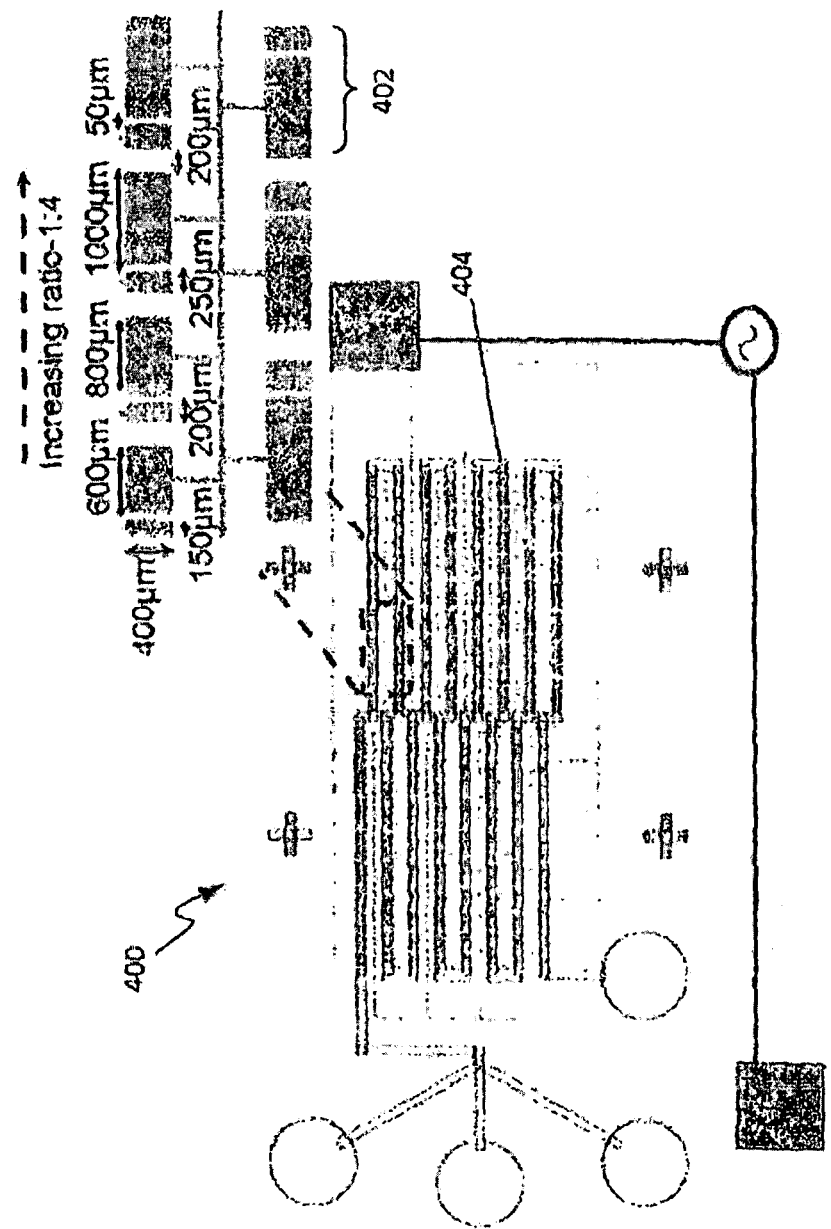

As shown in FIGS. 4 and 5, the second device type 400, identified herein as "EHD-µD2", is similar to the EHD-µD1 devices, but the dimensions of the asymmetric electrode pairs 402 increase along the serpentine channel 404, so that each successive electrode pair is larger than all of the preceding electrode pairs. These devices 400 contain 144 asymmetric planar electrode pairs 402 in a long serpentine channel 404, which again includes 16 interconnected elongate and mutually parallel segments, but with each segment containing only 9 electrode pairs 402. In each pair 402, the length of electrodes increases proportionally by maintaining a ratio of 1:4 (short:long). The same (inverse) ratio of $d_1/d_2=0.25$ is also maintained throughout the each segment of the channel, whilst the ratios $r_0/d_2$ and $r_1/d_2$ decrease with increasing electrode lengths.

Figure 7:
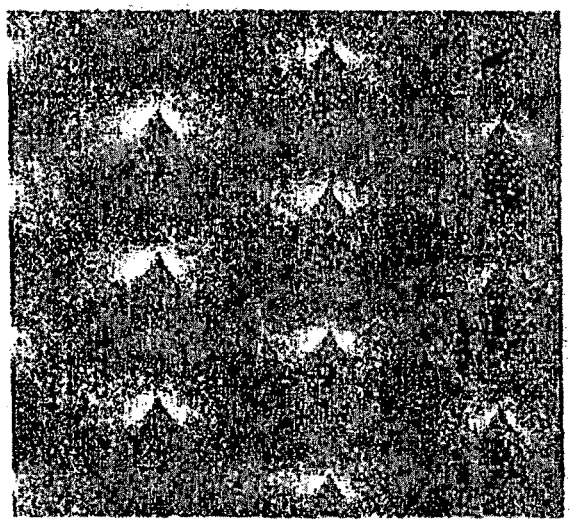
Figure 6:
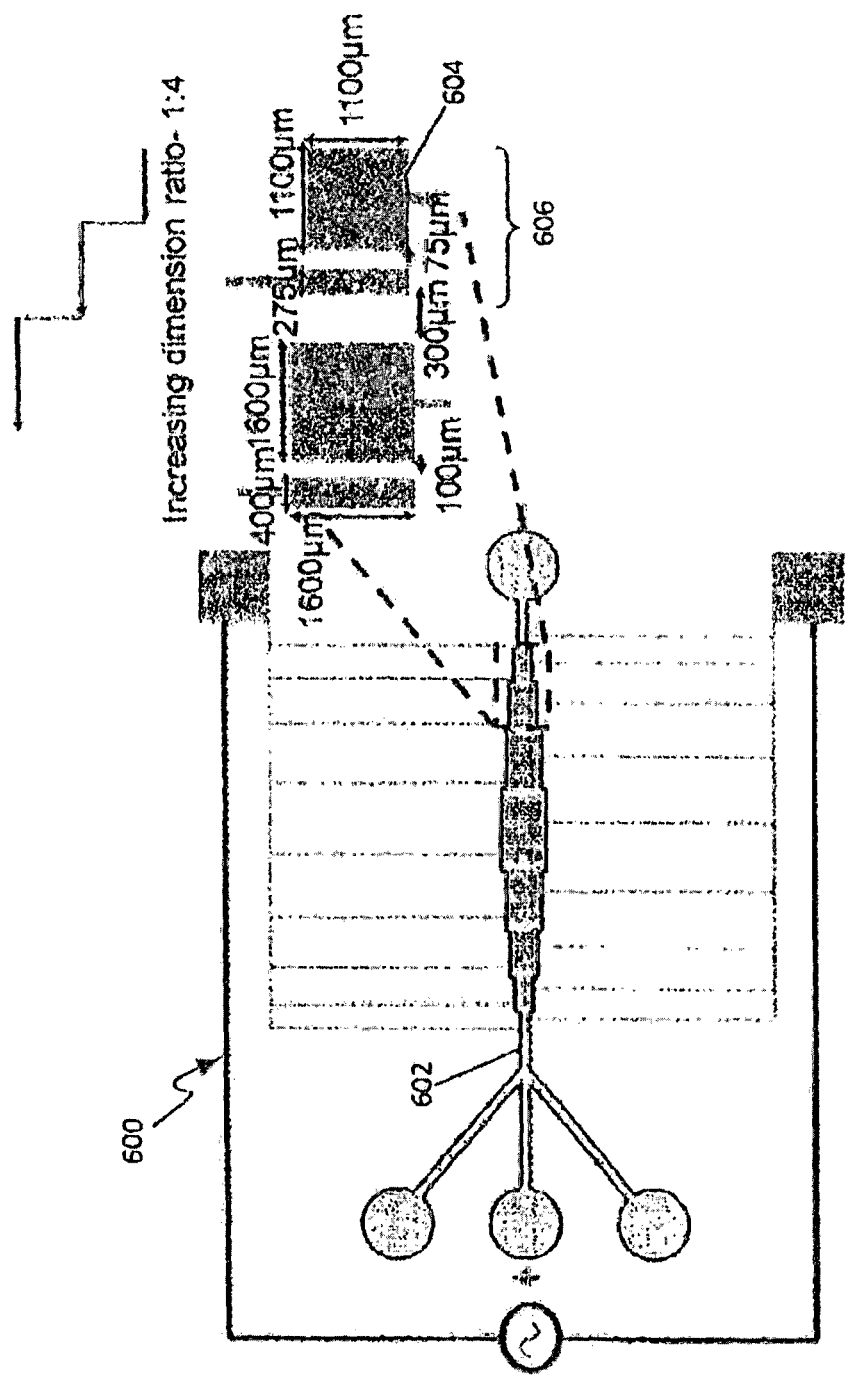

As shown in FIGS. 6 and 7, the third device type 600, identified herein as "EHD-µD3", has a linear channel 602 rather than a serpentine channel, and one electrode 604 (in this example, the long electrode) of each electrode pair 606 has a non-planar surface. In general, the non-planar surface includes features projecting into the fluidic channel to increase the surface area of the corresponding electrode and/or to improve mixing of the liquid sample. In the described embodiments, the nonplanar surface is a micromachined surface having features in the form of conical spikes/cones/tips projecting into the fluidic channel, as shown in the scanning electron microscope (SEM) image of FIG. 7. Each of these devices 600 contains 9 asymmetric electrode pairs 606 with a combination of planar and micromachined electrodes in a 22 mm-long channel 602. The electrode dimensions (length and width) both increase proportionally by maintaining a ratio of 1:4 (narrow:wide) along the first half of the channel 602 (from electrode pairs 1 to 5), and then correspondingly decrease in the second half of the channel 602 (from electrode pairs 6 to 9) by maintaining the inverse ratio. The ratio of $r_0/r_1$ also increases proportionally for pairs 1 to 5 and decreases by the inverse ratio for pairs 5 to 9. Thus, the dimensions of electrode pairs 1, 2, 3, and 4 are nominally the same as those of electrode pairs 9, 8, 7, and 6, respectively.

The micromachined surface features or 'microtips' have a base diameter of 150 µm. The microtips are arranged in a square array with a spacing of 100 µm between adjacent microtips. The total number of microtips on each electrode increases for electrode pairs 1 to 5 and decreases for electrode pairs 6 to 9. The fifth electrode pair has the largest number of tips (100 microtips in a 10×10 square array), and the first and ninth electrode pairs have the smallest number of tips (4 microtips in a 2×2 square array). Under an applied EHD field, the nonuniformity in geometric arrangement (e.g., planar and microtip) is believed to induce relatively complex fluid flows (e.g., microvortices) to enhance fluid mixing in the microchannel.

Although each of the devices described herein in detail and shown in the drawings has a particular combination of features (e.g., planar or non-planar electrodes, linear or serpentine fluidic channel configurations, and so on), many variations in the shape and/or configuration of the electrodes, the fluidic channel, and other features of the devices, and their combination in a device will be apparent to those skilled in the art in light of this disclosure, and alternative embodiments of the present invention may utilise such variations.

Figure 8:
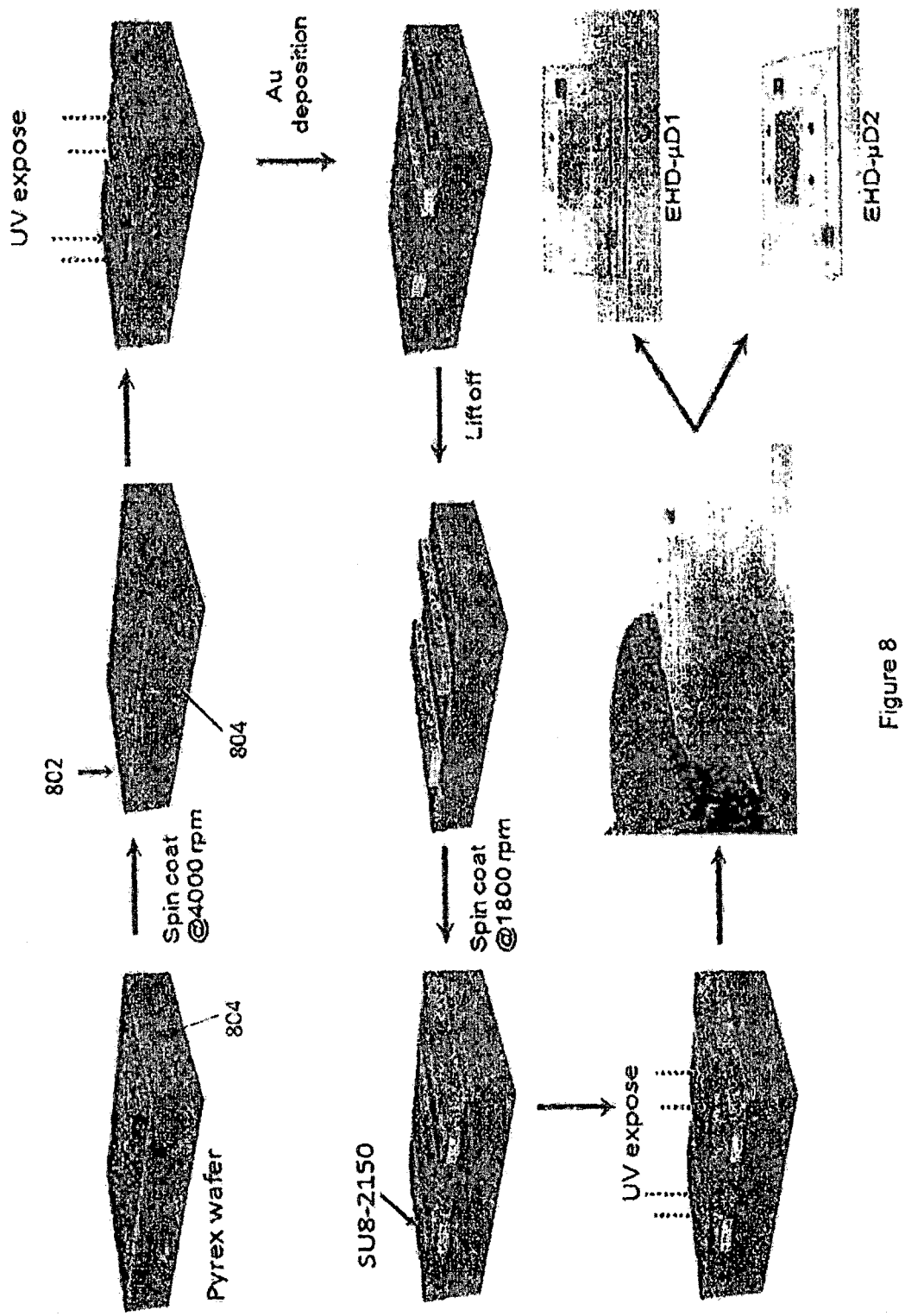
FIG. 8|Fabrication of EHD-μD1 and EHD-μD2 devices. Schematic illustration of EHD-μD1 and EHD-μD2 device fabrication steps FIG. 9|Layout editor design and strategy involved to remove SU-8 in between channel segments (marked in red) to achieve a final channel wall width of 100 μm.

All of the devices described above were fabricated at the Queensland node of the Australian National Fabrication Facility (Q-ANFF node). EHD-µD1 and EHD-µD2 devices were fabricated using a two-step photolithographic process, as shown in FIG. 8. In a first step, a thin film 802 of positive photoresist (AZ1518, Microchem, Newton, Calif.) was spin coated onto a pyrex glass wafer 804 (thickness, 1 mm). Subsequent photolithography using a MA6 mask aligner (UV exposure of 150 mJ/cm$^2$ and development with AZ 326MIF developer for 30 s) patterned the photoresist in preparation for electrode formation. Metallic layers of Ti (20 nm) and Au (200 nm) were then deposited using an electron beam (e-beam) evaporator (Temescal FC-2000) under high vacuum conditions, followed by acetone lift-off to define the electrode pairs 202, the contact pads 214, 216, and the interconnecting paths 202 therebetween.

In the second photolithography step, the serpentine channel (w=400 µm, h=300 µm) and inlet and outlet reservoirs were formed, by spin coating (1800 rpm) a layer of negative photoresist (Microchem, SU-8 2150) over the wafer with the patterned electrodes and then patterning it (using aligned photolithography) to remove the negative photoresist from the regions corresponding to the channels and reservoirs.

Figure 9:
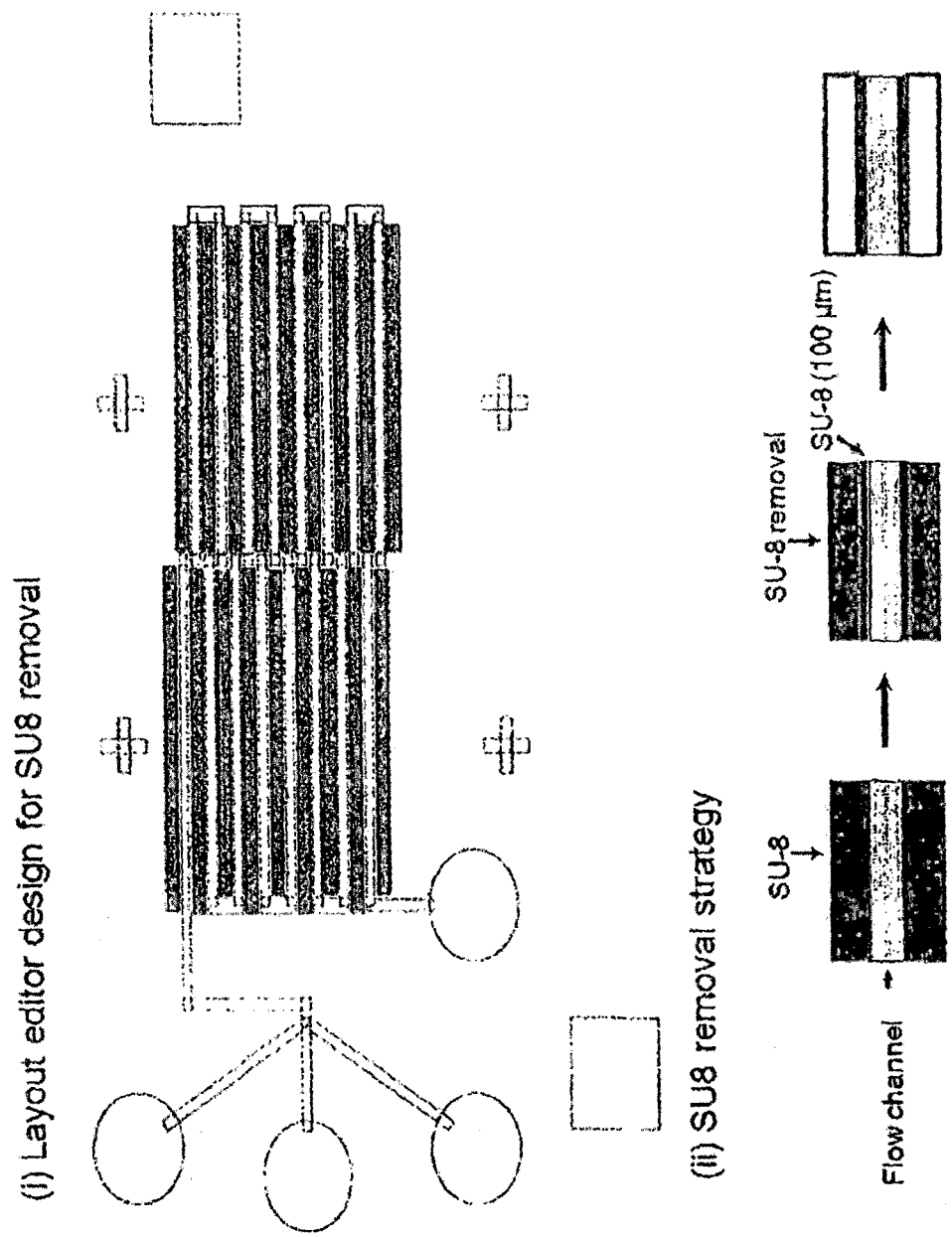

However, SU-8 photoresist has a strong auto-fluorescence. To reduce the auto-fluorescence of SU-8, the thickness of the channel walls is chosen to be thin by removing most of the SU-8 between the parallel segments of the channel to obtain a 100 µm-thick channel wall, as illustrated in FIG. 9. Soft and hard baking steps were performed as per manufacturer's instructions. Briefly, the wafer was soft baked through a series of step change in temperature (65° C. for 7 min→95° C. for 60 min→65° C. for 5 min) and followed by a post-bake step (from 65° C. for 5 min→95° C. for 20 min→65° C. for 3 min). Subsequent UV exposure (380 mJ/cm$^2$) and development in propylene glycol methyl ether acetate (PGMEA) for 45 min revealed the fluidic channel. The wafers were then hard baked and diced (ADT 7100 wafer precision dicer) to form individual devices. The channels of each device were then sealed with a 1 mm-thick glass coverslip having openings (diameter, 1.5 mm) to access the respective inlet and outlet reservoirs.

Figure 10:
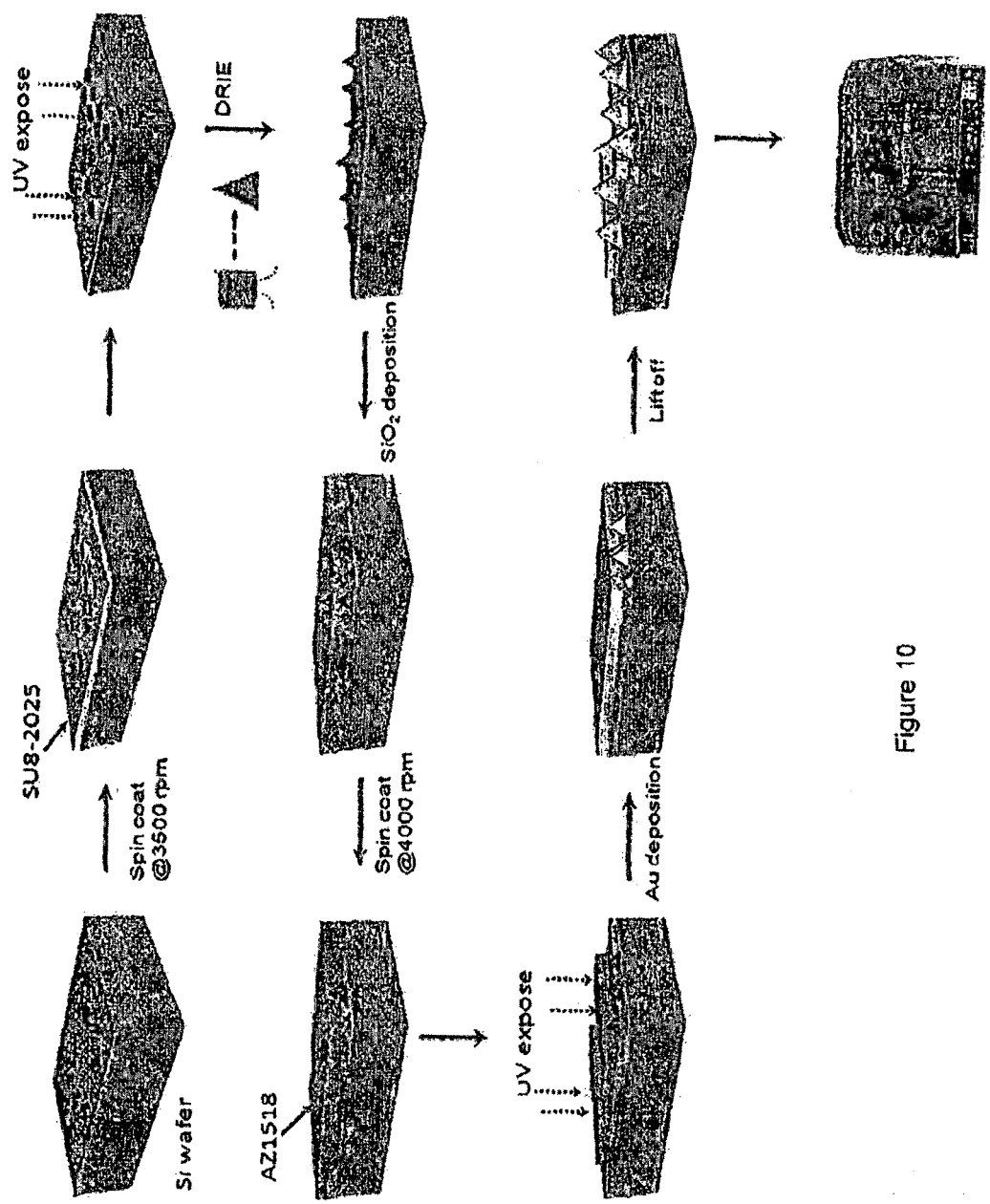
FIG. 10|Fabrication of EHD-μD3 devices. Schematic of EHD-μD3 device fabrication steps. Microtips were fabricated using a PlasmaTherm deep reactive ion etcher (DRIE).

The process steps involved in the fabrication of the EHD-µD3 devices are outlined in FIG. 10. For microtip fabrication, a 25 µm layer of negative photoresist (SU-8 2025, Microchem, Newton, Calif.) was spin coated (3500 rpm) onto a silicon wafer (diameter, 100 mm; thickness, 500 µm; single-side polished). A photomask containing circular patterns (diameter, 150 µm) for microtips in selected electrode regions (in this example, corresponding to the large electrode of each electrode pair) was transferred onto the photoresist layer. Subsequent UV exposure (250 mJ/cm$^2$) was followed by the development in propylene glycol methyl other acetate (PGMEA) step to remove any unexposed photoresist. Soft and hard baking steps were performed as per manufacturer's instructions. Briefly, the wafer was soft baked following temperature programming at through a series of step change in temperature (65° C. for 3 min→95° C. for 5 min→65° C. for 1 min) and followed by a post-bake step (from 65° C. for 1 min→95° C. for 3 min→65° C. for 1 min).

Microtips of approximately 85 µm high were fabricated using a PlasmaTherm deep reactive ion etcher (DRIE). DRIE conditions were optimized to reproducibly fabricate microtips. A passivation layer of silicon oxide (thickness, 100 nm) was then deposited on the etched wafer in an oxidation furnace. The wafer was cleaned with acetone/IPA and subsequently the two-step photolithographic process described above was performed, but of course using different masks to obtain the desired electrode pair and channel configuration, and being aligned to the microtips. In the described embodiment, these features are in rectangular arrays aligned to the channel (major flow) direction, so that the microtips in a given row shadow one another relative to the fluid flow. However, it will be apparent that arrays of these or other similar features could alternatively be misaligned with the channel/flow direction to enhance the degree of flow mixing and interaction, and/or the features could be randomly distributed over a part of the entirety of the surface of either or both of the electrodes in each pair. The wafers were diced into individual devices, bonded to glass cover slides, and sealed using glass coverslips.

In use, the small and large electrodes within the long channel of each EHD device were connected to a signal generator (Agilent 33220A Function Generator, Agilent Technologies, Inc., CA) via the gold contact pads (e.g., 216, 218).

The devices were characterized by SEM analysis using a JEOL (model 6610) instrument operating at an accelerating voltage of 10 kV. The EHD-µD3 devices were analysed at θ=60° and Z=20 mm using an operating voltage of 10 kV.

Each of the three device configurations described above allows relatively large sample volume throughput (>1 mL within 1 h) analysis that is ideally suited for CTC-related clinical settings. To demonstrate their effect on ac-EHD induced fluid flow, fluid flow visualization studies were performed by filling the inlet reservoirs with a solution of either 10 µm diameter fluorescent latex particles (Coulter Latron, USA) or a red dye, and the resulting flow was monitored using a high speed video camera fitted onto an upright microscope (Nikon Ni-U, Japan).

Figure 11:
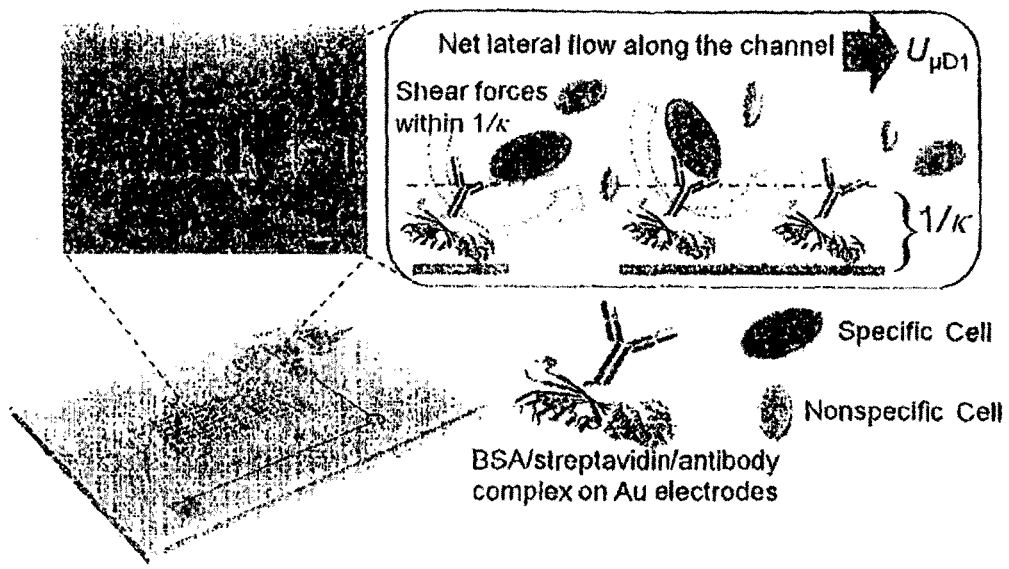
FIG. 11|ac-EHD induced fluid flow and micro- and nanoscopic shear forces for cell capture. A long array of asymmetric electrode pairs is fabricated in a serpentine microchannel containing 16 segments connecting each other with 16 electrode pairs in each segment (EHD-μD1). Upon application of ac BED field, a unidirectional fluid flow occurs, $U_{\mu D1}$, along the channel towards the larger electrode of each pair. This ac-EHD field also generates micro- and nanoscopic shear forces within the double layer (nanoshearing), which can shear away any non-specifically adsorbed cells and/or molecules.

In the EHD-µD1 devices, a unidirectional flow $U_{\mu D1}$, as shown schematically in FIG. 11, was observed, with the particles travelling from the smaller to larger electrode, and no particle movement observed in the absence of an applied field.

Figure 12:
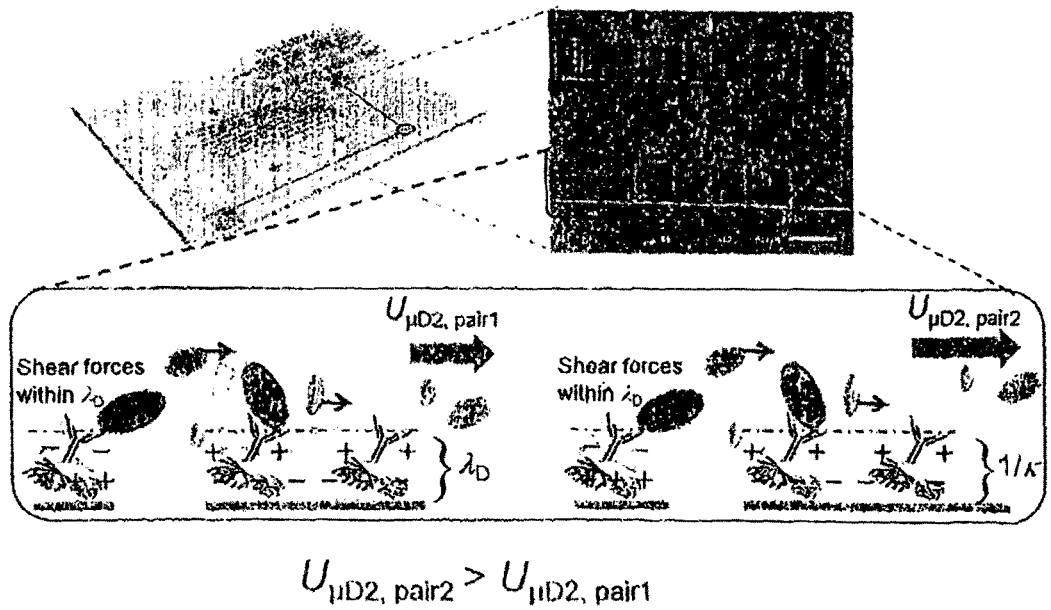
FIG. 12|ac-EHD induced fluid flow and micro and, nanoscopic shear forces for cell capture. A long array of asymmetric electrode pairs is fabricated in a serpentine microchannel containing 16 segments connecting each other with 9 electrode pairs in each segment (EHD-μD2). Upon application of ac EHD field, a lateral flow occurs, $U_{\mu D2, \, pair \, 1}$, along the channel in the direction of broken symmetry (e.g., towards the pair 2). This flow is predicted to increase with increasing electrode dimensions (e.g., $U_{\mu D2, \, pair2} > U_{\mu D2, \, pair1}$, $U_{\mu D2, \, pair3} > U_{\mu D2, \, pair2}$, so on), giving rise to acceleration in fluid flow across the channel. This enables control over micro/nanoscopic shear forces within the double layer, and control of the mixing and surface shear forces which enhance sensitivity and specificity of cell capture.

In the EHD-µD2 devices, the flow rate increases with increasing electrode dimensions, as illustrated in FIG. 12, giving rise to increasing flow velocity (i.e., $U_{\mu D2,\ pair2} > U_{\mu D2,\ pair1}$, $U_{\mu D2,\ pair3} > U_{\mu D2,\ pair2}$, and so on) towards the end of each elongate segment of the serpentine channel. The same behaviour was observed when a red dye solution was used instead of latex particles.

Figure 13:
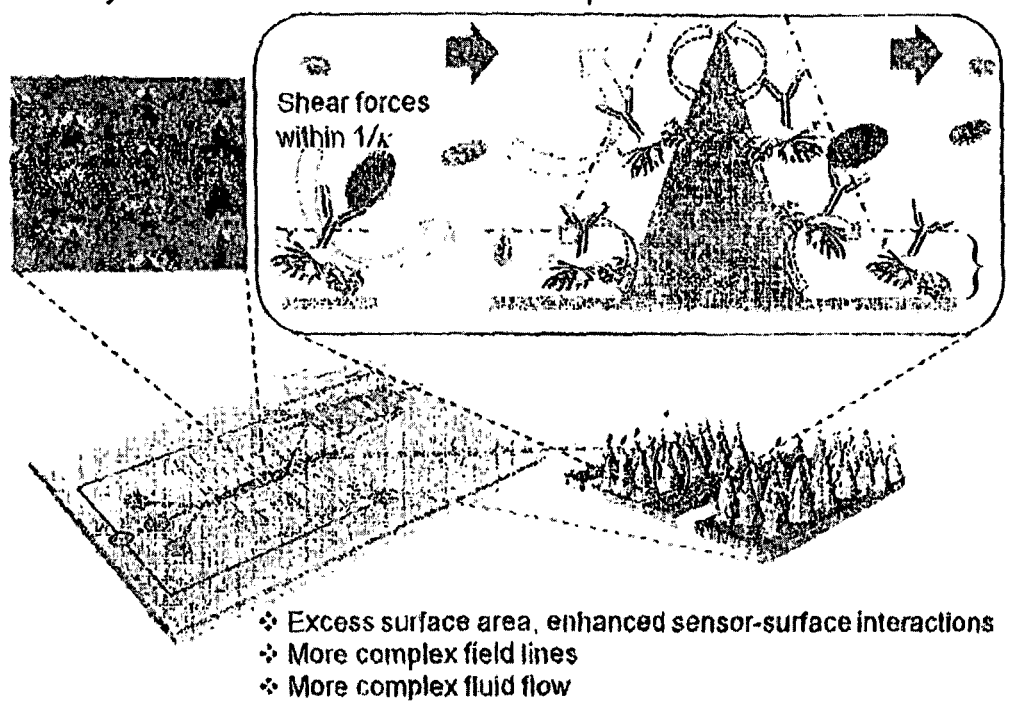
FIG. 13|An array of 9 asymmetric electrode pairs with a combination of planar and microtip electrodes was fabricated. Due to the presence of the additional spikes on the larger electrodes, the EHD-μD3 device creates more complex field lines, and thus, fluid exhibits complex flow movements. The arrow indicates the direction of objects movement along the fluids under ac-EHD field.

In the EHD-µD3 devices, the presence of microscale cones or tips facilitates the generation of complex fluid flow patterns, possibly including microscale vortices, as illustrated schematically in FIG. 13. This produces non-uniform local forces on the surfaces of the electrode that contribute to lateral or transverse flow across the fluidic channel, possibly resulting in chaotic fluid mixing. Additionally, the microscale tips are high aspect ratio structures with additional surface area and disrupt the streamlines to enhance fluid mixing, thereby increasing the number of particle-electrode interactions.

Figure 14:
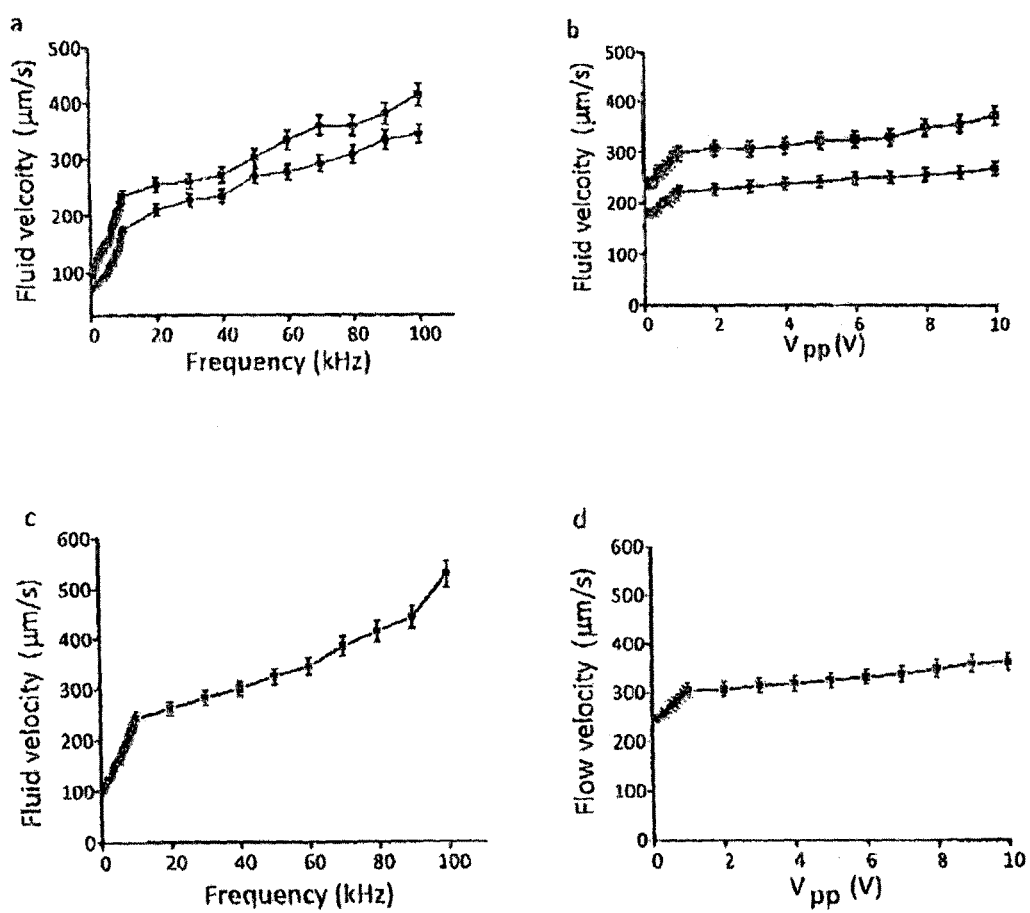
FIG. 14|Dependence of fluid velocity on the applied ac frequency at constant $V_{pp}$ (peak-to-peak voltage) (a, c) and applied $V_{pp}$ at constant frequency (b, d). The curves in FIGS. 14a and 14b are for the in EHD-μD1 (lower curve) and EHD-μD2 (upper curve) devices respectively.

As described above, the AC or DC signal that is used to generate the EHD field can be controlled to optimise the sensitivity and specificity of detection for rare CTCs. For example, FIG. 14 includes four graphs of the fluid velocity in the microfluidic channels as a function of (a, c) AC signal frequency of a sinusoidal signal having a peak-to-peak voltage or amplitude of 100 mV, and (b, d) as a function of the amplitude or peak-to-peak voltage $V_{pp}$ at a fixed frequency of 1 kHz. The upper curves in FIG. 14a and 14b are for the EHD-µD2 devices, and the lower curves are for the EHD-µD1 devices. These graphs indicate that the dependences of the fluid velocity on both the amplitude and on the frequency of the driving signal are both bimodal, with each graph displaying two approximately linear sections, the dependence being relatively strong at values of these parameters below respective threshold values (of about 10 kHz and 1V), and relatively weakly dependent at higher values of the corresponding parameter. Additionally, whereas the fluid velocity is only weakly dependent on the signal amplitude for amplitudes in excess of ~1V, it remains significantly dependent on a signal frequency up to at least 100 kHz. For this reason, the signal frequency was chosen as the adjustable parameter to control the fluid velocity (and hence shear forces and mixing), at a constant amplitude or peak-to-peak voltage.

To determine the optimal ac-EHD signal frequency for CTC capture, capture efficiencies of the three device types were determined, using whole cells expressing Human Epidermal Growth Factor Receptor 2 (HER2), an important biomarker of breast cancer and a major therapeutic target as described in Vaidyanathan, R., Shiddiky, M. J. A., Rauf, S., Dray, E., Tay, Z. & Trau, M., *Tuneable "Nano-Shearing": A Physical Mechanism to Displace Nonspecific Cell Adhesion During Rare Cell Detection*, Anal. Chem. 86, 2042-2049; DOI: 10.1021/ac4032516 (2014); Vaidyanathan, R., Rauf, S., Dray, E., Shiddiky, M. J. A. & Trau, M., *Alternating current Electrohydrodynamics Induced "Nanoshearing" and Fluid Micromixing for Specific Capture of Cancer cells*, Chem. Eur. J. 20; DOI: 10.1002/chem201304590 (2014) and its Supplementary Information, the entirety of both documents being incorporated herein by reference. The samples were prepared by spiking pre-stained HER2(+) cells (e.g., MCF7) into PBS buffer and were electro-hydrodynamically pumped through the anti-HER2 functionalized devices using an AC signal frequency range of 0.6-100 kHz at constant $V_{pp}$ (100 mV; for Vpp>100 mV, the fluid flow attained almost near steady state).

Figure 15:
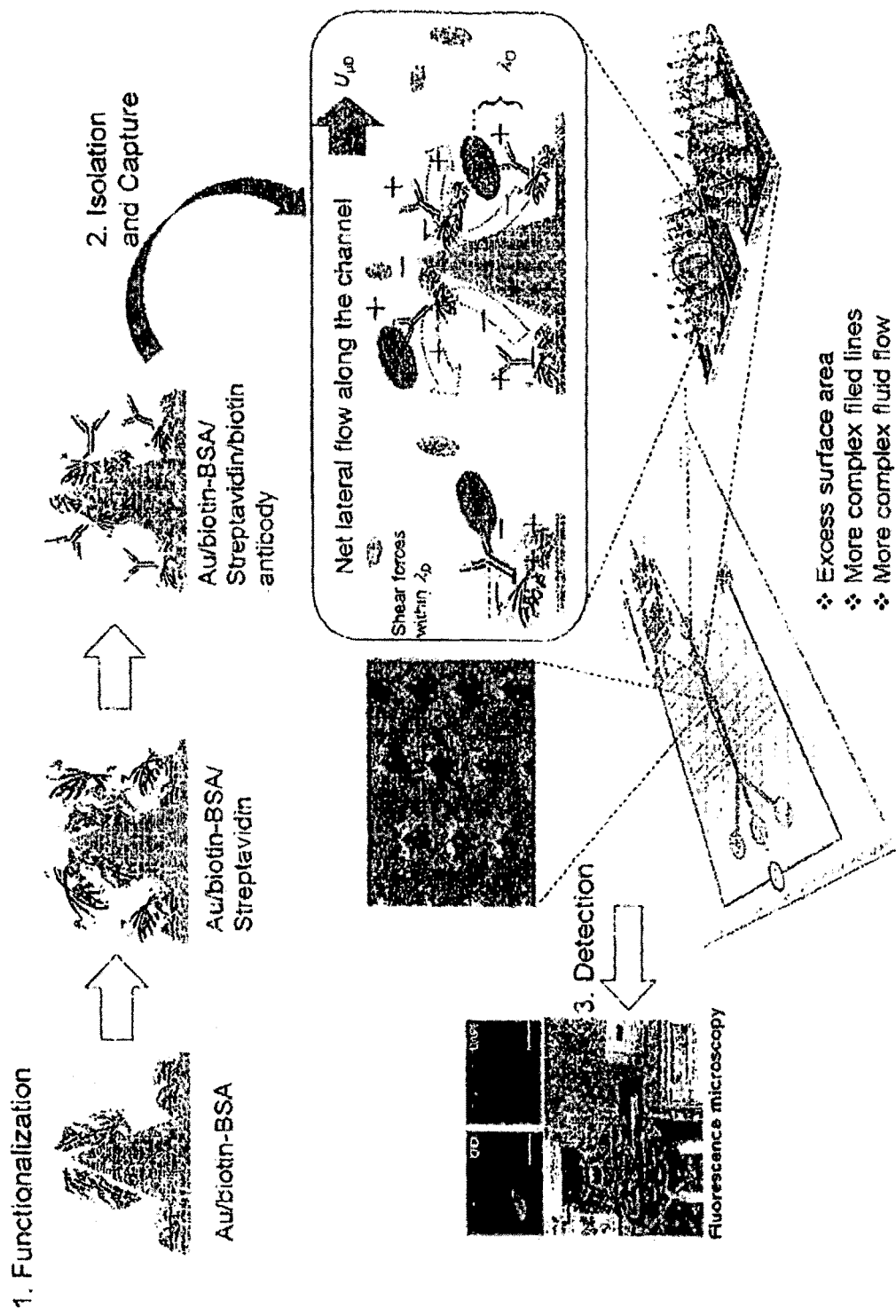
FIG. 15|Device functionalization. Schematic representation of cell capture and detection.

Each device was functionalised as follows. The gold microelectrode pairs within the capture domain of the fluidic channel were modified with anti-HER2 using avidin-biotin chemistry, as shown in FIG. 15. The electrodes were cleaned by sonication in acetone for 5 min, rinsed with isopropyl alcohol and water for another 2 min, and dried in flowing nitrogen. They were then incubated in biotinylated BSA (200 µg/mL in PBS, Invitrogen) solution for 2 hours, followed by coupling with streptavidin (100 µg/mL in PBS, Invitrogen) for 1 h at 37° C. The streptavidin conjugated channels were coated with biotinylated anti-HER2 (100 µg/ml in PBS, R&D systems) for another 2 h. After each of these three functionalising steps, the channel was flushed three times with PBS (10 mM, pH 7.0) to remove any unbonded molecules.

The cells were labelled as follows. HER2+ (MCF7 and T-47D) and HER2− (MDA MB-231) breast cancer cell lines were all obtained from American Type Culture Collection (ATCC) and maintained in Dulbeccos Modified Eagles Medium (DMEM; Sigma, UK) supplemented with 10% fetal bovine serum (FBS), 1% Penicillin/streptomycin, 0.5% insulin and 0.5% sodium pyruvate, and 5% $CO_2$ at 37° C. Before experiments, cells were cultured according to the standard procedure described in Pratt, S. E. & Pollak, M. N., *Estrogen and antiestrogen modulation of MCF7 human breast cancer cell proliferation is associated with specific alterations in accumulation of insulin-like growth factor-binding proteins in conditioned media*, Cancer Res. 53, 5193-5198 (1993). The cultured cells were trypsinized and counted using a particle counter (Beckman Coulter, US) to obtain the desired cell density upon dilution. MCF7 or T-47D cells (100,000 cells/sample) were labelled with 5 µL of DiD+ fluorescent dye (Invitrogen, UK) and incubated at 37° C. for 20 min. The desired concentration of cells was then prepared by serial dilution in PBS (10 mM, pH 7.0).

A 1 mL aliquot of sample spiked in buffer was placed into the inlet reservoirs of the devices and driven through the channel by applying an ac-EHD field. The EHD field was applied for periods of 30 min interleaved with 15 min intervals (without an ac-EHD field), for a total period of 2 hours. Control experiments were performed under static conditions (without an ac-EHD field) by filling the device with spiked samples, and incubated for 2 h. Captured cells were fixed by filling the device with cold methanol for 10 min, permeabilized with 0.2% Triton X-100 in PBS for 10 min, and subsequently stained with DAPI solution for 20 min. The devices were then flushed three times with PBS by applying the ac-EHD field to remove any unbonded molecules after each step. Images were taken by using a multichannel fluorescence microscope (Nikon Ti-U upright microscope, Melville, N.Y.) using dual stains (DiD-red and DAPI-blue) and analyzed by image processing software (Nikon Ni-S elements, Basic Research). For counting captured MCF7 and T-47 D cells (<1000 cells mL$^{-1}$), the devices were analyzed under a brightfield microscope (Nikon Ti-U upright microscope, Melville, N.Y.). For control experiments involving only MDA MB-231 cells ($10^5$ cellsmL$^{-1}$), captured cells were trypsinized to recover them from the devices and counted using a particle counter.

Figure 16:
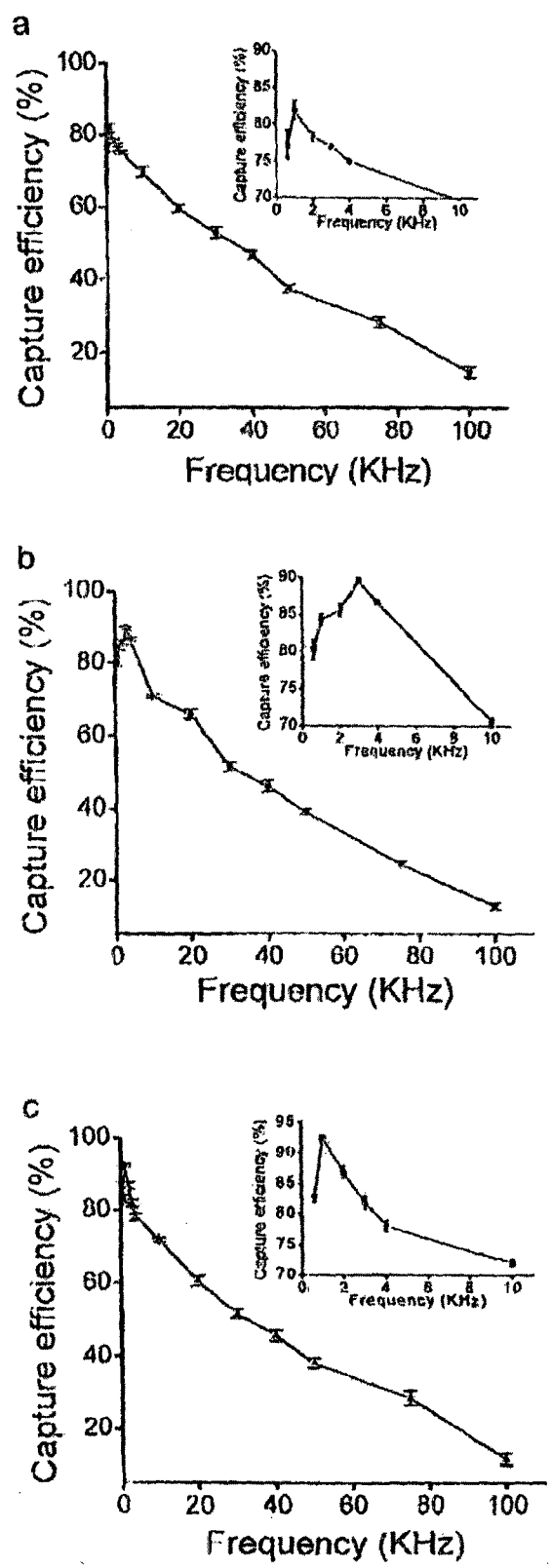
FIG. 16|Cell capture under different ac-EHD fields. Capture efficiency from PBS (10 mM, pH 7.4) spiked with HER2 (+) (200 cells/mL) in a, EHD-μD1, b, EHD-μD2, c, EHD-μD3 as a function of applied frequency at constant $V_{pp}$. The optimal ac-EHD frequencies for each of the devices were determined as 1, 3, and 1 kHz at 100 mV ($V_{pp}$) for EHD-μD1, EHD-μD2, and EHD-μD3, respectively.

For all three device types, the initial capture efficiency was found to increase sharply, then decrease gradually with increasing frequency, as shown in FIG. 16. These results can be explained by considering the ac-EHD induced fluid flow and manipulation of shear forces within the thin double layer (e.g., $1/\kappa$, ≈2 mm under these conditions). At lower frequencies, stimulation of the fluid flow around the sensors can increase the effective cell-antibody collisions (and under conditions where the shear forces are less than the antibody-cell binding force), thereby resulting in high capture efficiency. At higher frequencies, cell-antibody bonding does not occur effectively due to the stronger fluid flow (and under conditions where shear forces exceed the antibody-cell binding force) which could wash out many cells and decrease the capture efficiency of the device.

As shown in FIGS. 16(a), (b), and (c), the optimum signal frequencies for the EHD-µD1, EHD-µD2, and EHD-µD3 devices were respectively 1 kHz, 3 kHz, and 1 kHz at 100 mV ($V_{pp}$), for which the respective capture efficiencies were about 85, 90, and 93%.

Figure 17:
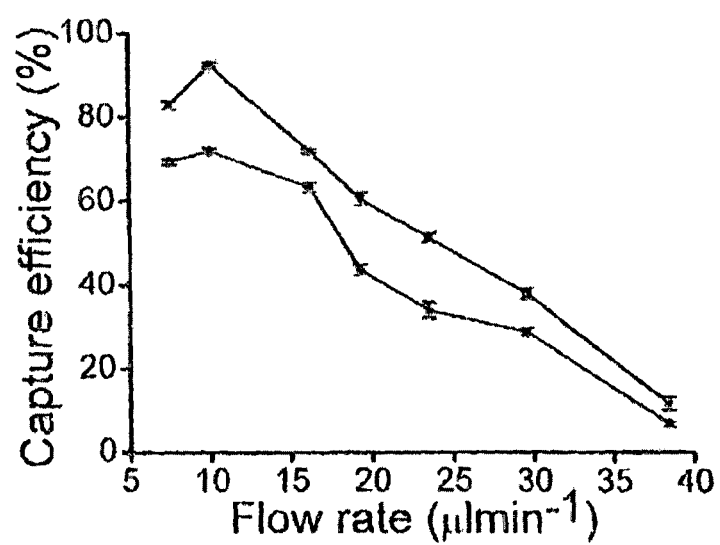
FIG. 17 Capture efficiency from PBS (10 mM, pH 7.0) spiked with MCF7 (200 cellsmL$^{-1}$) in EHD-μD2 at different flow rate under ac-EHD (upper curve) and pressure driven flow (lower curve) conditions. The ac-EHD field strength of f=600 Hz to 100 kHz at constant $V_{pp}$=100 mV generates fluid flow equivalent to 7.5 (600 Hz) to 38.5 μL min$^{-1}$ (100 kHz) (calculated based on the time required to flow 1 mL of blood under ac-EHD field).
Figure 18:
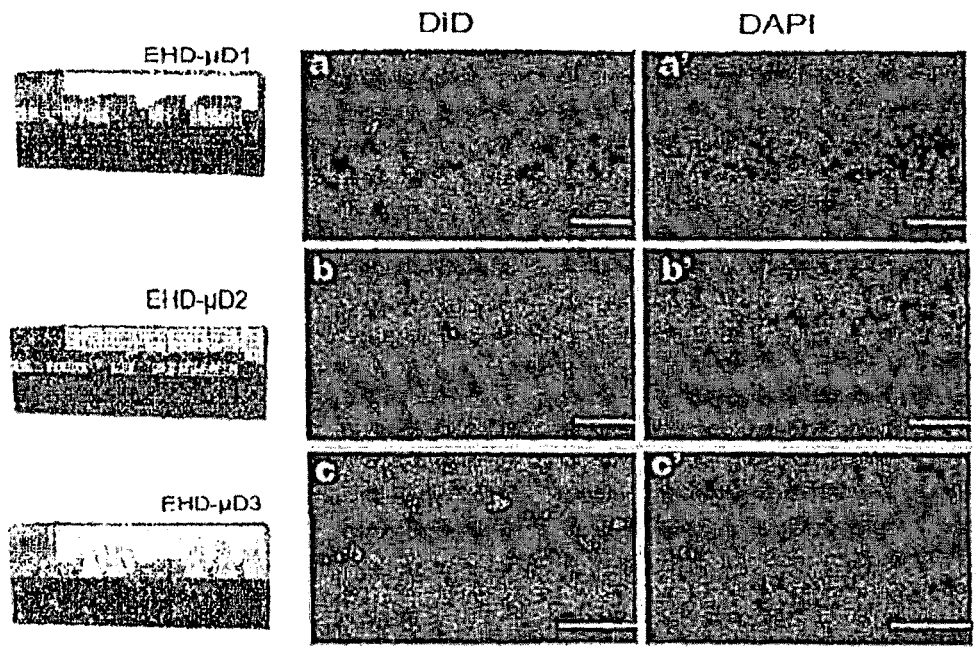
FIGS. 18 and 19|Fluorescence images of captured HER2+ cells. The MCF7 cells pre-stained with DiD and DAPI were captured from PBS (FIG. 18) and lysed blood (FIG. 19) spiked with 200 cells/mL using EHD-μD1 (a, a', d, d'), (b, b', e, e'), and EHD-μD3 (c, c', f, f') devices. Scale bar is 100 μm.
Figure 19:
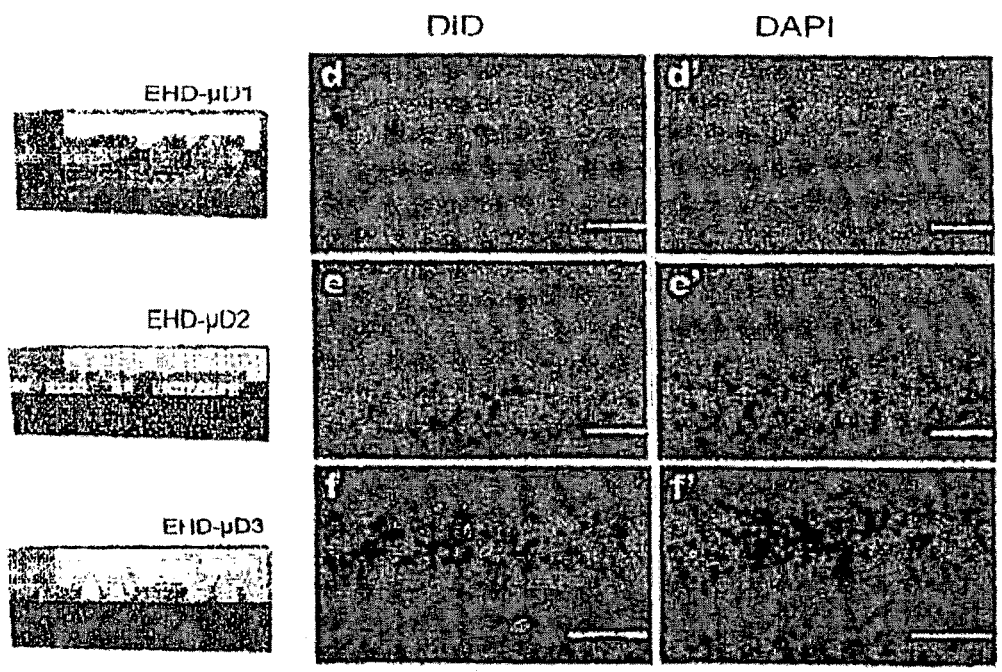

We also compared the capture efficiency of the device under different ac-EHD flow rates with those obtained under pressure-driven flow (via a syringe pump) of the same flow Rates, as shown in FIG. 17. MCF7 cells (200 cells mL$^{-1}$) were spiked in PBS and run on anti-HER2 functionalized devices under different ac-EHD flow rates obtained using the field strength of f=600 to 100 kHz at constant $V_{pp}$=100 mV. The equivalent flow rates calculated on the basis of the lime required to flow 1 mL of blood under the ac-EHD field was 7.5-38.5 µL min$^{-1}$, and these flow rates were used for pressure-driven flow experiments. Unlike ac-EHD case, the capture efficiency under the pressure-driven flow system was found to increase slowly at low flow rates (at <10 µL min$^{-1}$). Under the optimal flow condition (i.e., 10 µL min$^{-1}$ which is equivalent to the flow rate generated under the ac-EHD field strength of f=1 kHz and $V_{pp}$=100 mV), an approximately 20±1.04% increase in capture efficiency (92+0.76% versus 72±0.57%) for ac-EHD devices was achieved compared to that of pressure driven flow. At >10 µL min$^{-1}$, the capture efficiency decreases gradually with increasing flow rates. However, a significant enhancement in capture efficiency across all operating ac-EHD flow rates was observed in comparison to pressure driven flows. This enhanced capture efficiency under ac-EHD induced fluid flow is presumably owing to the additional effective manipulation of shear forces (i.e., nanoshearing) and concomitant fluid nixing that can augment the specific capture of cells due to increased number of effective cell-surface (antibody functionalized) collisions.

Figure 20:
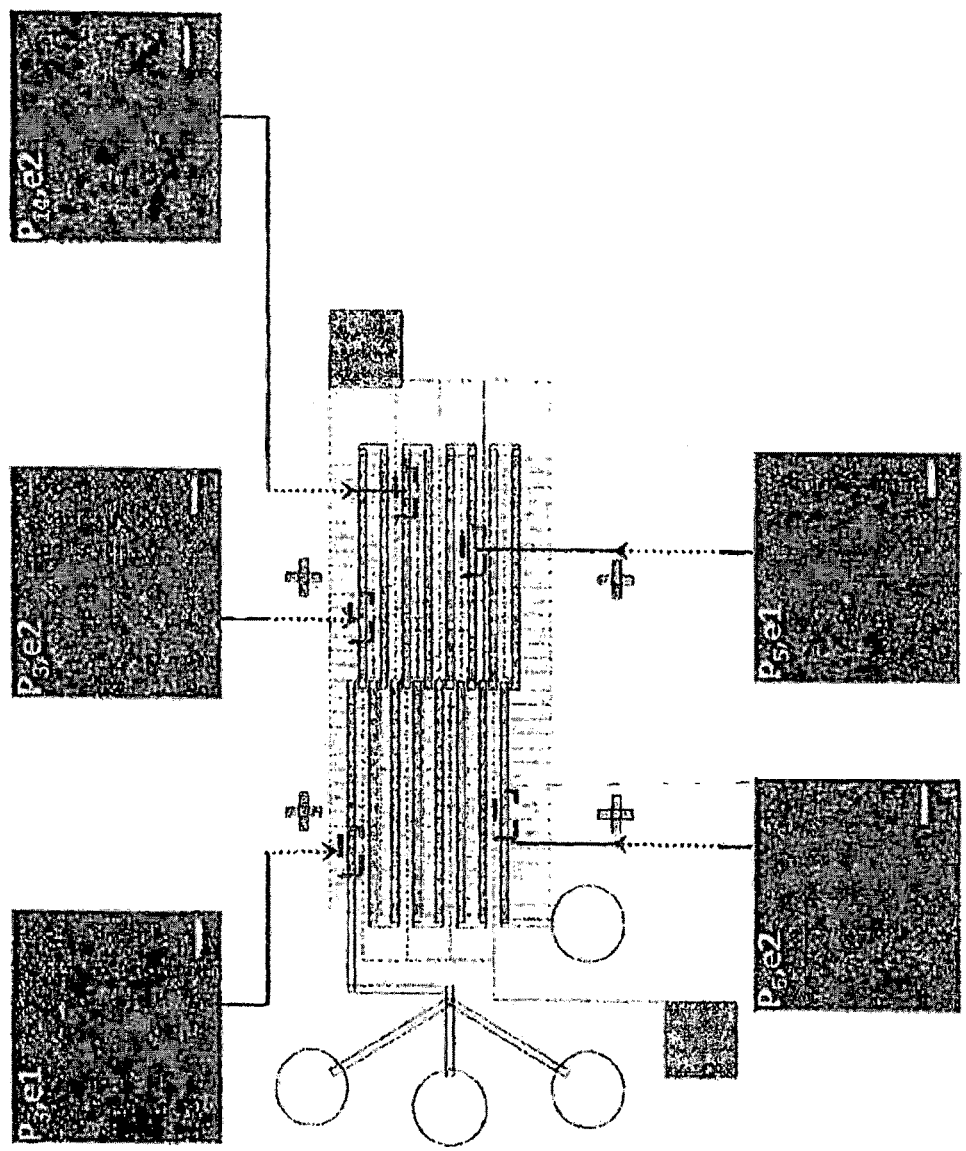
FIGS. 20 and 21|Cells distribution in devices. The distribution of captured MCF7 cells under optimal ac-EHD conditions in the EHD-μD1 (FIG. 14) and EHD-μD2 (FIG. 15) devices. The captured cells were more spread throughout the EHD-μD1 device, whereas the majority of cells were captured within the first 5 segments of the EHD-μD2 device Scale bar: 100 μm.
Figure 21:
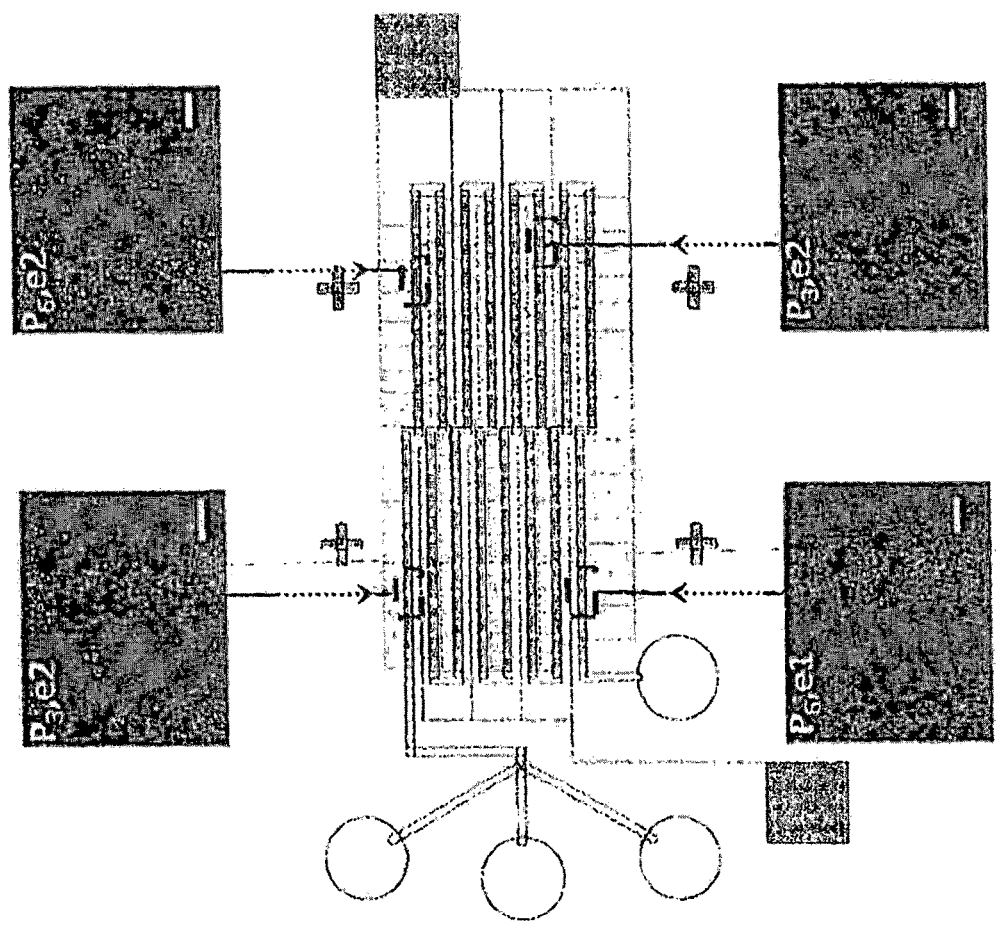
Figure 22:
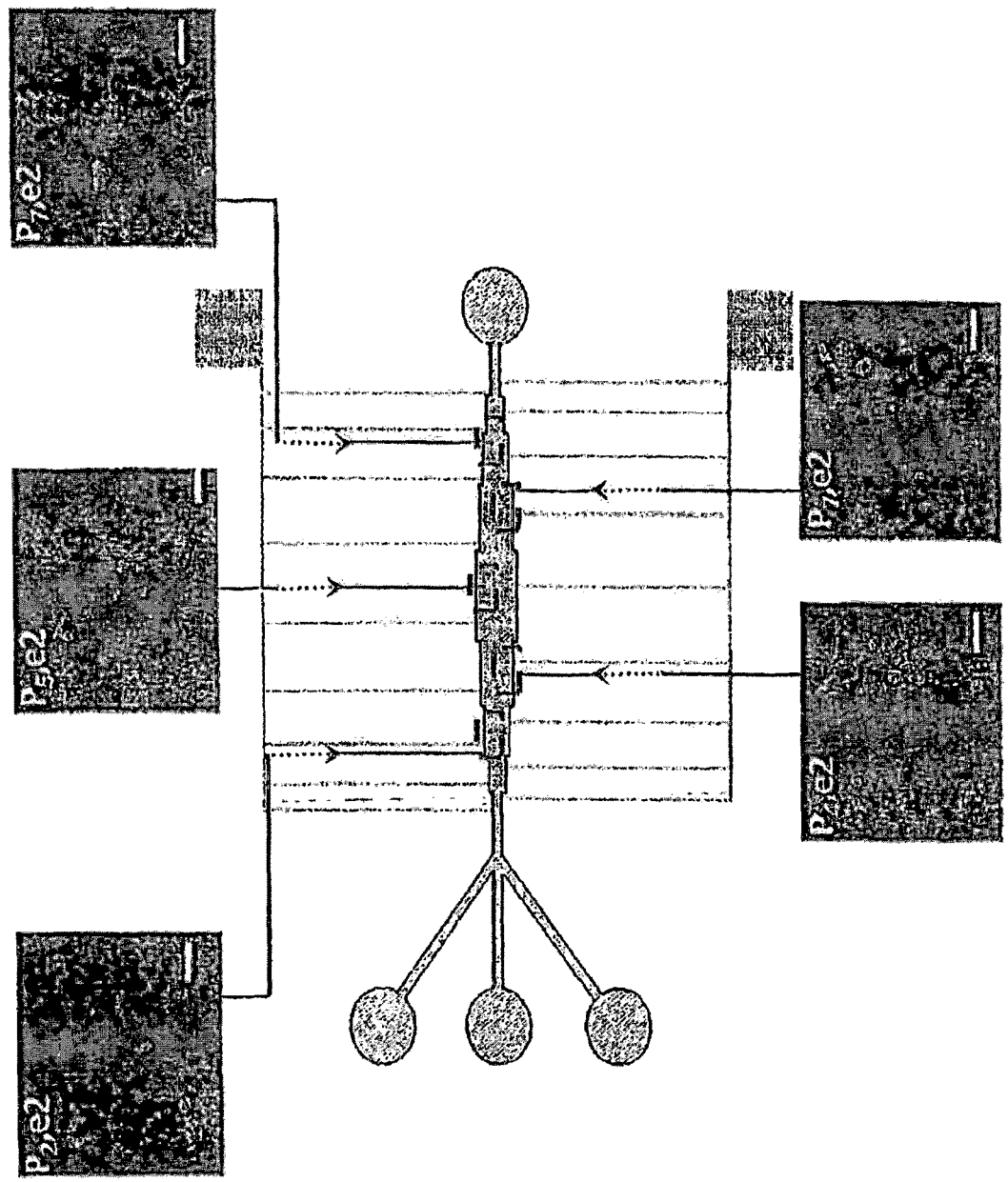
FIG. 22|Cell distribution in devices. The distribution of captured MCF7 cells under optimal ac-EHD conditions in EHD-μD3 device. The majority of the cells were captured between electrode pairs 3 to 5. Scale bar: 50 μm.

Typical images of captured cells are shown in FIGS. 18 to 22. In EHD-µD1 devices, the spatial distribution of cells was fairly uniform throughout the serpentine channel, as shown in FIG. 20, whereas in the EHD-µD2 devices, the majority of cells were captured within the first five segments of the channel, as shown in FIG. 21. As shown in FIG. 22, in the EHD-µD3 devices, the majority of the captured cells were captured by the third to filth electrode pairs, which are located towards the centre of the channel where its width is greatest.

Figure 23:
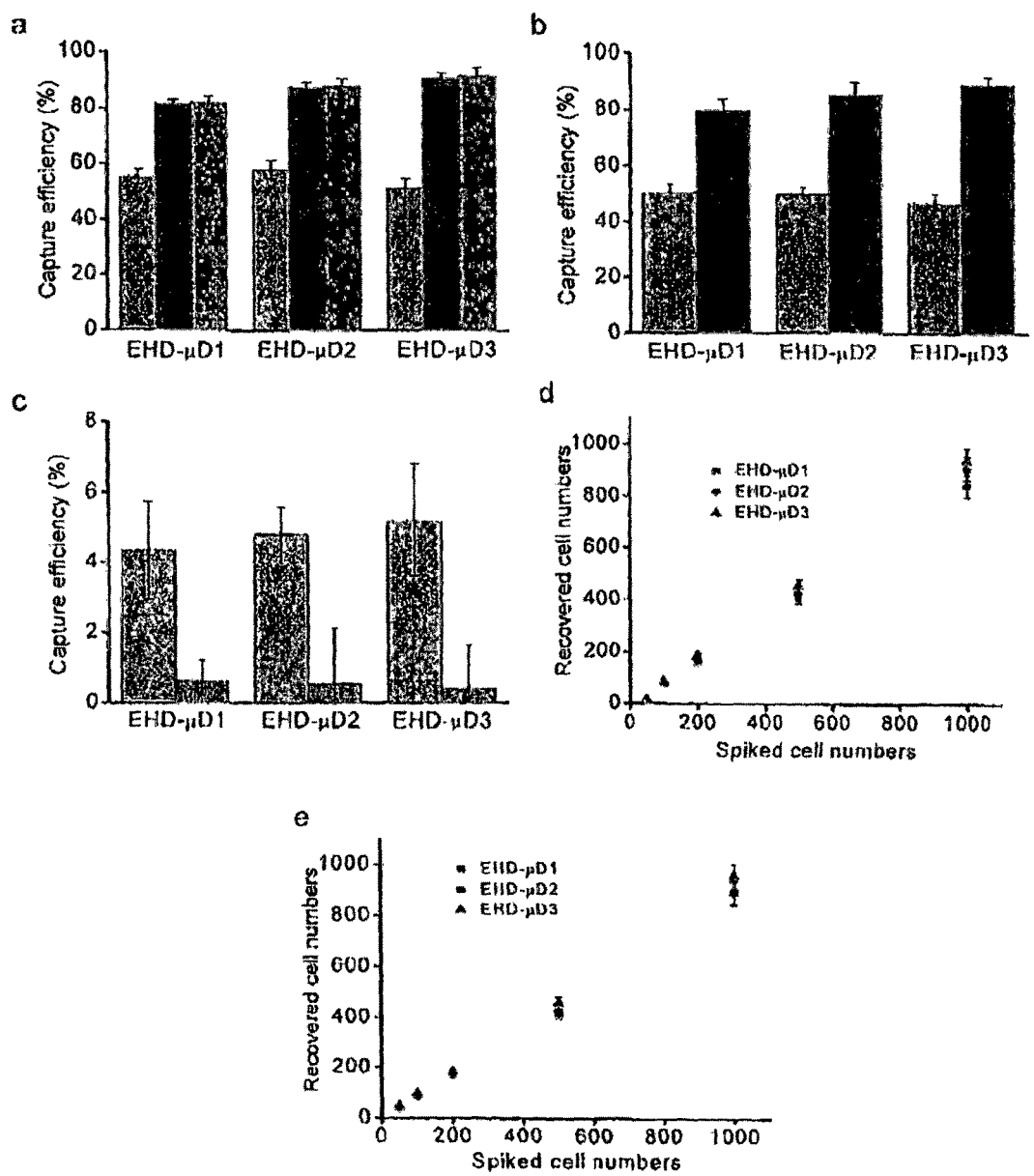
FIG. 23|Cell capture using ac-EHD devices. a,b Capture efficiency from PBS (10 mM, pH 7.4) spiked with MCF7 (200 cellsmL$^{-1}$; central bar in a) and 200 cellsmL$^{-1}$ T-47D (right hand bar in a), and 100000 cellsmL$^{-1}$ MDA-MB-231+ 200 cellsmL$^{-1}$ MCF7 (black bar) cell lines. The light grey left hand bars in (a) and (b) represent data for control experiments from PBS buffer spiked with 200 cellsmL$^{-1}$ MCF7 (a) and 100000 cellsmL$^{-1}$ MDA-MB-231+200 cellsmL$^{-1}$ MCF7 (b) with no ac-EHD field. c, Capture efficiency from PBS (10 mM, pH 7.4) spiked with prestained MDA-MB-231 (100000 cellsmL$^{-1}$) with (right hand bar in c) and without (left hand bar in c) ac-EHD field. d,e, Capture efficiency from PBS (d) and lysed blood (e) spiked with 50-1000 MCF7 cells mL$^{-1}$. Each data point represents the average of three separate trials and error bars represent standard error of measurements within each experiment.

To investigate the contribution of the EHD process to the measured capture efficiencies, the experiments were repeated in the same devices, but with no signals applied to the electrodes, the fluid remaining static within the microfluidic channels for 2 hours. FIG. 23 compares the results of these control experiments with the results obtained using ac-EHD to pump the fluid samples through the microfluidic channels, using the optimum signal frequency values and other conditions described above.

As shown in FIG. 23(a), the control devices (e.g., without EHD, gray histogram bars) resulted in capture efficiencies of 56% (EHD-µD1), 56.5% (EHD-µD2) and 51% (EHD-µD3), which are about 35% lower than the capture efficiencies obtained from the same devices and identical conditions except that the sample liquid was pumped by the ac-EHD field at the optimum frequency (blue histogram bars). The observed improvement in capture efficiency is believed to result from enhanced mixing in the fluidic channel, thereby increasing the probability of binding interactions between the cells and their counterpart antibodies. The highest capture efficiency (e.g., 93%) observed in the EHD-µD3 devices is attributed to the additional mixing enhancing cell-antibody collisions and thus attachment, due to the presence of the microscale tips on the electrodes.

To investigate whether the capture efficiencies are different for different target cell types (but using the same antibody), a different HER2(+) target cell (T-47 D) was captured using the optimal ac-EHD signal frequency determined above. As shown in FIG. 23(a), the capture efficiencies of 200 T-47 D cells mL$^{-1}$ (red histogram bars) was similar to the corresponding capture efficiencies of the 200 MCF/cells mL$^{-1}$ (blue histogram bars), suggesting that the capture efficiencies are insensitive to the specific cell type for the same antibody.

The cell capture specificity of the ac-EHD devices was demonstrated by spiking pre-stained MCF7 (200 cellsmL$^{-1}$) along with HER2(−) MDA-MB-231 cells ($10^5$ cellsmL$^{-1}$). As shown in FIG. 22(b), the MCF7 carfare efficiency (black histogram bars) in all three devices decreased by only 5% (compare with the blue histogram bars in FIG. 23(a)) in the presence of a 500-fold larger background of MDA MB-231 cells (in a sample containing 200 MCF7 cells mL$^{-1}$ and 100,000 MDA MB-231 cells mL$^{-1}$), indicating their good specificity in detecting target cells in the presence of a large excess of non-target cells.

Additionally, control devices (without an ac-EHD field) yielded a >8% reduction in capture efficiency (gray bars in FIG. 23(b)) for these mixed samples (MCF7+MDA-MB-231 cells) in comparison to those obtained for only MCF7 cells (gray bars in FIG. 23(a)), presumably due to the non-specific adsorption of MDA-MB-231 cells on the Sensing electrodes.

To examine the effect of EHD on the non-specific adsorption of cells, another control experiment using pre-stained MDA-MB-231 cells (100000 cells mL$^{-1}$) spiked in PBS was performed in the presence and absence of an ac-EHD field. As shown in FIG. 23(c), the ac-EHD field (green histogram bars) caused an approximately ten-fold decrease in the capture efficiency of nonspecific MDA-MB-231 cells in comparison to the controls (gray bars), indicating that MID is highly effective in reducing non-specific cell adsortion, presumably by generating shear forces large enough to shear away loosely adhered non-specific cells from the antibody-coated electrode surfaces.

Figure 24:
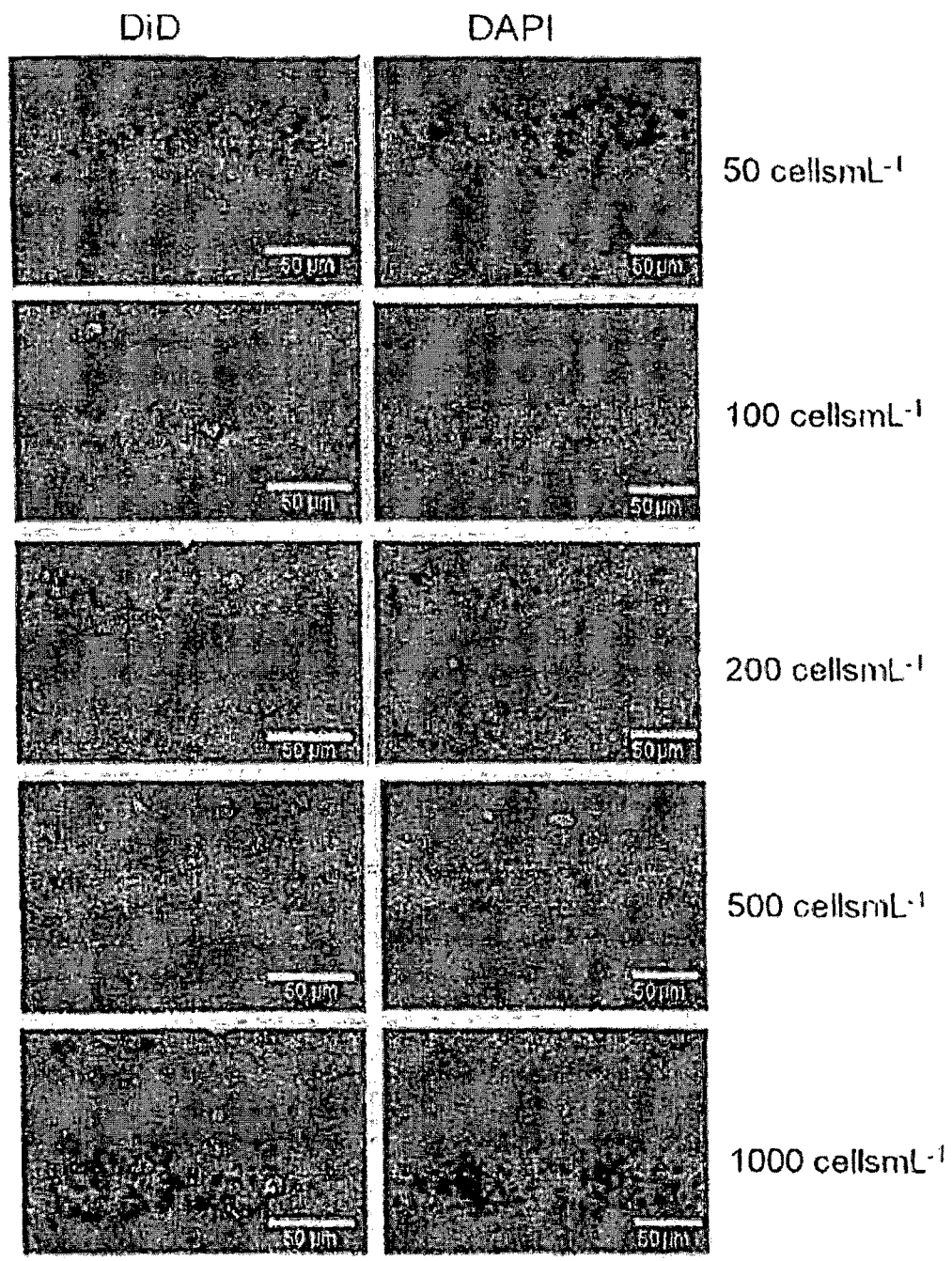
FIG. 24|Fluorescence analysis of HER2+ cell capture under ac-EHD field. Representative images of cell-capture in EHD-μD3 (electrode pair 3) using samples containing MCF7 cells spiked in PBS at designated cell concentrations ranging from 50-1000 cellsmL$^{-1}$.

To test the sensitivity of detection, MCF7 cells were spiked in a PBS buffer at concentrations ranging from 50 to 1000 cells mL$^{-1}$. Under the optimal ac-EHD conditions described above, all three device types yielded capture efficiencies of about 70% for EHD-µD1 whilst the recovery for the EHD-µD2 and EHD-µD3 devices were 79% and 86% respectively for samples containing 50 cells mL$^{-1}$, the capture efficiencies gradually increasing with increasing cell populations in the sample solutions, as shown in FIG. 23(d). The capture efficiencies of the EHD-µD1, EHD-µD2, and EHD-µD3 devices were about 83, 88, and 92%, respectively, for samples containing >200 cells mL$^{-1}$. Images of the captured cells for different sample concentrations are shown in FIG. 24.

To validate the analytical performance of these devices under more physiological conditions, the capture of target cells from lysed rat blood was measured. Whole rat blood samples were obtained from the animal house at the AIBN (the Australian Institute for Bioengineering and Nanotechnology), The University of Queensland. RBC lysis buffer (pH 7.5) was added to blood in 10:1 v/v ratio, and mixed for 20 min at room temperature. After centrifugation at 1000 rpm for 5 min, the supernatant was removed and the cell pellet was re-suspended in an equivalent volume of buffer. Designated concentrations of DiD+ labelled MCF7 cells were then spiked into lysed blood.

The lysed rat blood was spiked with MCF7 cells at concentrations ranging from 50 to 1000 cells mL$^{-1}$. As shown in FIG. 23(e), under the optimal ac field conditions described above, a capture efficiency 40% was attained for the seed level of 50 cells mL$^{-1}$ in EHD-µD1, whilst the capture efficiencies for EHD-µD2 and EHD-µD3 devices were 42% and 48%, respectively. It was also noted that the devices exhibited about 5% lower capture efficiency for lysed blood samples containing >100 cells mL$^{-1}$ in comparison with buffer. However, the high level of capture efficiency obtained in blood samples (e.g, <1000 MCF7 cells in the presence of millions of white blood cells, platelets and other molecules) indicate that the method is highly suitable for blood sample analysis.

The high capture efficiency observed in EHD-µD3 in comparison to EHD-µD1 and EHD-µD2 could be attributed to additional micromixing due to the presence of the microtips that enhanced the number of cell-antibody collisions. Therefore, EHD-µD3 was used for further studies in demonstrating the application of ac-EHD induced nanoshearing to the specific capture of low numbers of cancer cells in blood samples.

Figure 25:
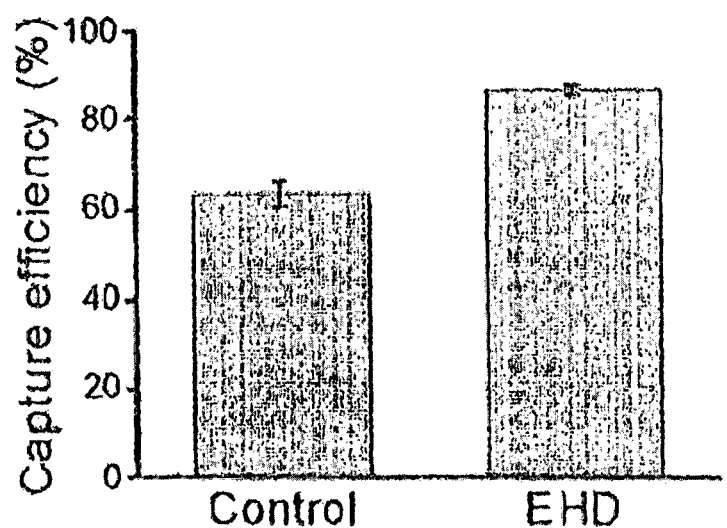
FIG. 25|Capture efficiency in EHD-μD3 from 10× diluted blood spiked with prestained BT-474 cells (500 cells mL$^{-1}$) under ac-EHD and pressure-driven flow (control; flow rate=10 μL min$^{-1}$) conditions.

To validate the capture efficiency of the EHD devices in complex heterogeneous samples, HER2(+) BT-474 cells were spiked in 1 mL of 10× diluted blood samples and experiments were performed using a EHD-µD3 device. Under the optimal ac field strength of f=1 kHz and $V_{pp}$=100 mV, the capture efficiency was found to be 37±1.5% (FIG. 25). Control devices operated under a pressure driven flow rate of 10 µL min$^{-1}$ resulted in capture efficiency of 63±4.7%. An approximately 24% increase in capture efficiency with the use of ac-EHD induced fluid flow compared to pressure driven flow was achieved, which is attributed to additional "nanoshearing" anti concomitant fluid micromixing.

Figure 26:
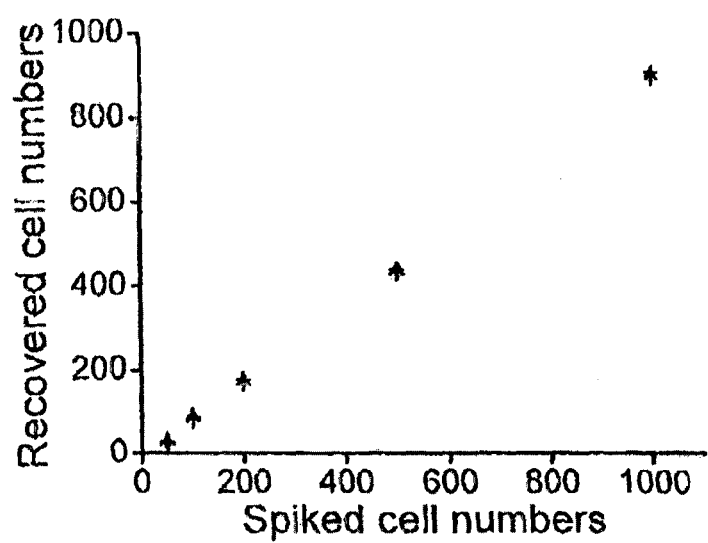
FIG. 26|Recovered cell numbers from 10× diluted blood spiked with pre-stained 50-1000 BT-474 cellsmL$^{-1}$ under ac-EHD in EHD-μD2. Each data point represents the average of three separate trials (n=3) and error bars represent standard error of measurements within each experiment.

To assess the dynamic range of detection, BT-474 cells ranging from 50 to 1000 cells were spiked in 10× diluted blood, as shown in FIG. 26. Under the optimal ac-EHD condition, the recovery for the seed level of 50 cells mL$^{-1}$ was 53±4.39% and capture efficiency was 86±2.74% for samples containing >100 cells. This level of capture efficiency obtained from blood samples (e.g., 86±2.74% for 100-1000 BT-474 cells in large excess of nonspecific cells including WBCs, RBCs, platelets and oilier molecules) indicate that the devices described herein can be used for the efficient recovery of low cell numbers from complex heterogeneous samples without sample pre-processing.

Figure 27:
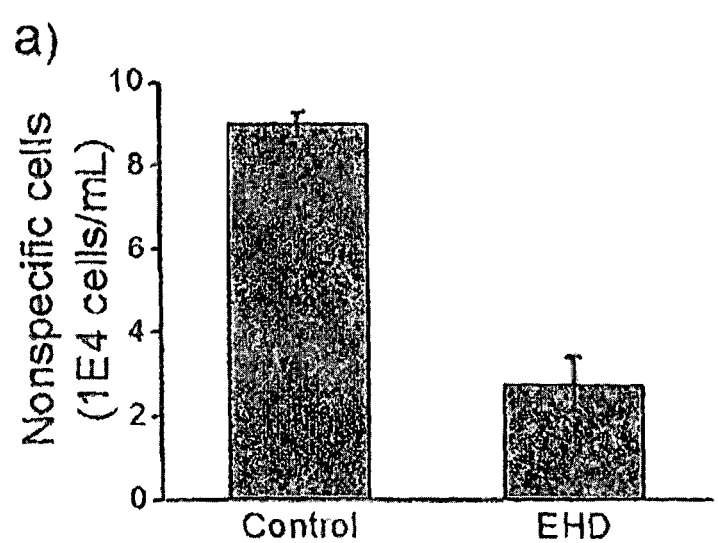
FIG. 27|Number of nonspecific cells recovered from 10× diluted blood under ac-EHD (f=1 kHz and V$_{pp}$=100 mV) and pressure driven flow (control; flow rate=10 μLmin$^{-1}$) conditions in EHD-μD2.

To demonstrate the utility of the nanoshearing phenomena in removing weakly bound cells present in blood samples, experiments were performed using 10× diluted blood samples in EHD-µD3 under the optimal ac-EHD field (e.g., f=1 kHz, $V_{pp}$=100 mV) in comparison with pressure driven fluid flow based control devices. Pressure-driven flow based control experiments were performed using a syringe pump at similar flow rate to that of ac-EHD. In the presence of ac-EHD, an approximately 4-fold reduction in the number of nonspecific blood cells that adhere to the electrode surface in comparison to the control device was observed, as shown in FIG. 27. This data demonstrate that "nanoshearing" phenomenon is highly effective in reducing nonspecific adsorption of cells.

In order to quantify the average purity of the isolated cell population (i.e., percentage ratio of captured DiD+ BT-474 cells to the nonspecifically bound CD45+WBCs), 500 BT-474 cells were spiked in 1 ml of 10× diluted blood. An approximately 5-fold enhancement in capture purity in ac-EHD devices compared to that of pressure-driven flow based devices (22±5.24% versus 4±3.6%) was observed. This is probably due to the ability of ac-EHD induced nanoshearing to shear away nonspecifically bound blood cells from the electrode surface. A similar level of capture purity for blood samples has been demonstrated elsewhere using hydrodynamic flow and size based technologies. Further optimization of the protocol and device geometry (e.g., length, width, and height of the channel; shape, size, and arrangement of the microtips; spacing between electrodes in the long array of asymmetric pairs within the channel) may improve the capture purity of the devices described herein.

Finally, the utility of the devices to recover viable cells was tested using Trypan blue exclusion experiments upon recovery via TrypLE treatment 11. BT-474 cells (5×10⁴ cells) were spiked in PBS and captured in anti-HER2 functionalized devices under the optimal ac-EHD field. Trypan blue staining of the recovered cells resulted in >90% cell viability in EHD-µD2, suggesting that the described approach can facilitate further molecular characterization of the recovered cells.

Example II—Protein Detection

To demonstrate the use oldie described nanoshearing effect for molecular target detection, the capture and detection of human epidermal growth factor receptor 2 (HER2) antigen spiked into PBS or human serum was investigated, as described in Shiddiky, M. J. A., Vaidyanathan, R., Rauf, S., Tay, Z. & Trau, M., *Molecular Nanoshearing: An Innovative Approach to Shear off Molecules with AC-Induced Nanoscopic Fluid Flow*, Sci. Rep. 4, 3716; DOI:10.1038/srep03716 (2014) and its Supplementary Information, the entirety of both documents being incorporated herein by reference.

Serum samples were collected from healthy volunteers and upon estimation of total protein using standard Bradford method, designated concentrations of Human ErbB2/HER2 protein spiked in PBS or scrum was placed in to the inlet reservoirs of the devices and driven through the channel by applying ac-EHD field. The held strength was applied for 30 min with 15 min intervals (without fluid flow) for a total pumping time of 2 h. Control experiments were performed in the absence of ac-EHD field under pressure driven flow conditions using a syringe pump (PHD 2000, Harvard apparatus). Detection antibody FITC conjugated anti-HBR2 (2 µgmL$^{-1}$) and/or Alexafluor 633 anti-IgG (2 µgmL$^{-1}$) was driven through the channel under ac-EHD and/or pressure driven flow conditions. Devices were washed repeatedly in PBS and imaged under a fluorescence microscope (Nikon eclipse Ni-U upright microscope). Image analysis was performed using the image processing software (Nikon Ni-S elements, Basic Research) by considering a region of interest to obtain a count of the fluorescence, spots based on fluorescence intensity range, size and circularity. The intensity range for the particular wavelength (e.g., FITC, AlexaFluor) was set based on the mean intensity. The length scale chosen was set to scan spots <1 µm during the analysis. For comprehensive and improved data analysis, images were captured on similar electrode pairs for each device during individual trials and the 400 µm×400 µm region of interest was maintained.

Figure 28:
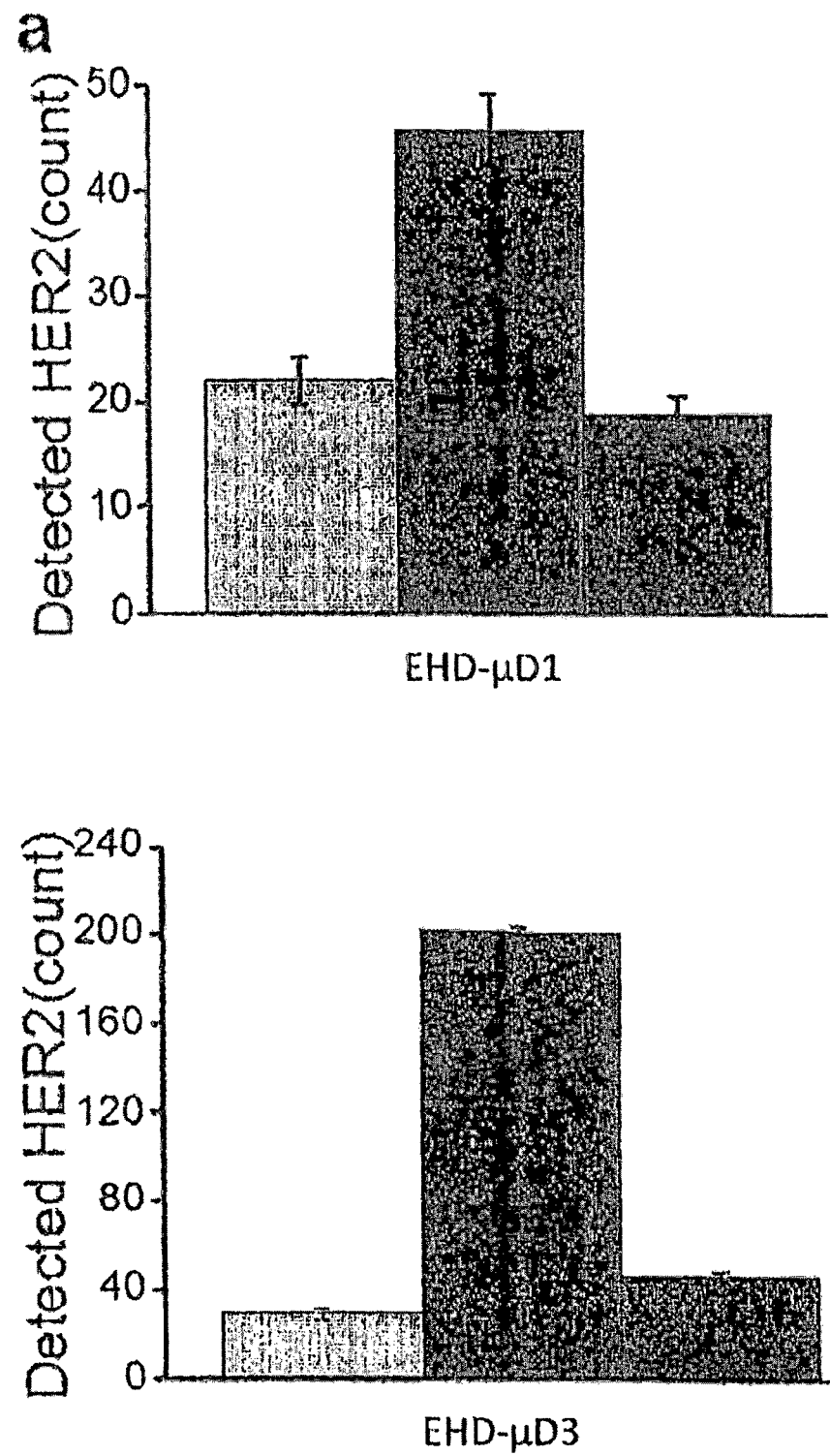
FIG. 28|Fluorescence imaging of the captured HER2 protein at different ac field conditions. (a,b) Fluorescence image analysis of HER2 (100 pgmL$^{-1}$ spiked in PBS) capture at the frequency of f=600 Hz (central bar) and 100 kHz (right hand bar) at V$_{pp}$=100 mV in (a) EHD-μD1 and (b) EHD-μD3. Control devices (left hand bar) include those tested under pressure driven flow conditions. Pressure driven flow based devices operated under the rate of 10 μLmin$^{-1}$ (an equivalent flow rate of that calculated based on the time required to flow 1 mL of sample under the given ac-EHD field). Each data point represents the average of three separate trials (n=3) and error bars represent standard error of measurements within each experiment.
Figure 29:
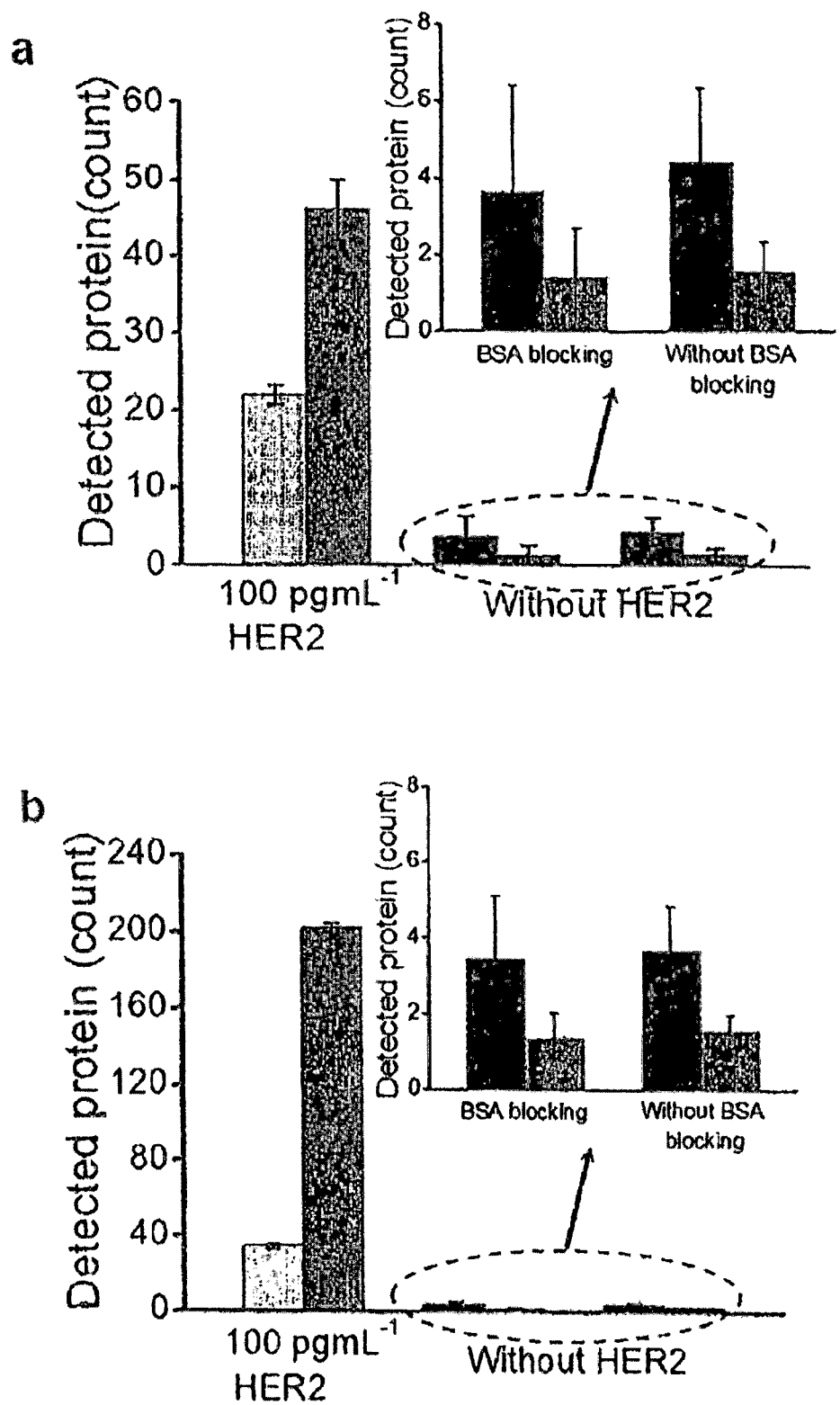
FIG. 29|Specificity and accuracy of immunocapture. (a,b) Fluorescence image analysis of proteins from human serum spiked with (100 pgmL$^{-1}$; light gray (control), dark gray) and without HER2 under ac-EHD (f=1 kHz, V$_{pp}$=100 mV) and pressure driven (control) flow condition in (a) EHD-μD1 and (b) EHD-μD3. Inset shows fluorescence image analysis of proteins from human serum without HER2 on anti-HER2-functionalized devices blocked with (black, control; green, ac-EHD) and without (blue, control; red, ac-EHD) BSA. Pressure driven flow based devices operated under the rate of 10 μLmin$^{-1}$ (an equivalent flow rate of that calculated based on the time required to flow 1 mL of scrum samples under the given ac-EHD field). Each data point represents the average of three separate trials (n=3) and error bars represent standard error of measurements within each experiment.

Serum samples were run on anti-HER2 functionalized (as described above) devices using a signal frequency (f) range of 600 Hz-100 kHz at constant amplitude ($V_{pp}$) of 100 mV. FIGS. 28 and 29 include histograms showing the results of typical fluorescence image analysis obtained using devices EHD-µD1 (FIGS. 28($a$) and 29($a$)) and EHD-µD3 (FIGS. 28($b$) and 29($b$)) for 100 pgmL$^{-1}$ HER2 antigen spiked in PBS at a signal frequency of 600 Hz (black bars) and 100 kHz (red bars) at $V_{pp}$=100 mV applied across each electrode pair, with a control result (without ac-EHD; light gray bars) also shown for comparison. The capture performance of both devices operating at a frequency of 600 Hz was found to be significantly Increased (2-fold for EHD-µD1 and 3-fold in EHD-µD3) in comparison to that the performance al 100 kHz.

These data indicate that the protein capture performance of the described devices is a function of the frequency of the applied. AC field. The resulting high level of capture at relatively low field frequency is probably due to the stimulation of the fluid flow around the anti-HER2 functionalized electrodes, which can maximize the effective protein-antibody binding (a condition where shear force<antibody-antigen binding force).

In contrast, at high field frequency (e.g., f=100 kHz, $V_{pp}$=100 mV), protein-antibody binding does not occur as effectively due to the stronger fluid flow (a condition where shear forces>antibody-antigen affinity interaction), which could decrease HER2 antigen recognition and thus decrease the capture level. The microtips in the EHD-µD3 are high aspect ratio structures with additional surface area and disrupt the streamlines to induce better fluid mixing, thereby increasing the number of antibody-antigen interactions which leads to increased capture performance. Therefore, a relatively low field frequency (e.g., f=1 kHz, $V_{pp}$=100 mV) was used for further studies in demonstrating the application of ac-EHD induced nanoshearing phenomenon for the detection of proteins.

Control experiments to compare the capture performance of the devices under ac-EHD flow to that of a hydrodynamic flow were performed using a pressure-driven system (via a syringe pump) to drive fluid through the devices with the similar flow rate. Fluorescence images of the capture of 100 pgmL$^{-1}$ HER2 under various conditions were acquired and analysed. Under the ac-EHD field conditions, the devices yielded a 2 (EHD-µD1) and 6-fold (EHD-µD3) higher capture yields in comparison with the devices operating under hydrodynamic flow conditions. This high capture yield is presumably owing to the ac-EHD induced fluid flow and manipulation of the shear forces within the double layer, which could maximize the effective antibody-antigen affinity interaction.

To validate the specificity and accuracy of the immunocapture, control experiments were performed using serum samples spiked with (100 µgmL$^{-1}$) and without HER2. Under the field strength of f=1 kHz and $V_{pp}$=100 mV, negligible nonspecific binding of the detection antibody was observed in both ac-EHD (dark-gray versus red bars in FIGS. 29($a$), ($b$) devices. Furthermore, approximately 2.5 (EHD-µD1) and 5-fold (EHD-µD3) enhancement in the detection capabilities was observed under ac-EHD in comparison to the hydrodynamic flow based control devices. To investigate the effect of BSA blocking on detection capabilities of the devices, additional control experiments were performed using BSA blocked anti-HER2 functionalized devices. Serum samples without HER2 antigens were driven through the devices under both ac-EHD and hydrodynamic flow conditions.

As eau be seen in the insets of FIG. 29$a$, $b$. BSA blocking did not have a substantial effect in altering detection capabilities of the devices (similar nonspecific binding of the detection antibody) in comparison to the devices without BSA blocking. This data suggests that ac-EHD induced nanoshearing can enhance the detection capabilities of the devices by enhancing the specificity of capture and accuracy of the immunoassay.

Figure 30:
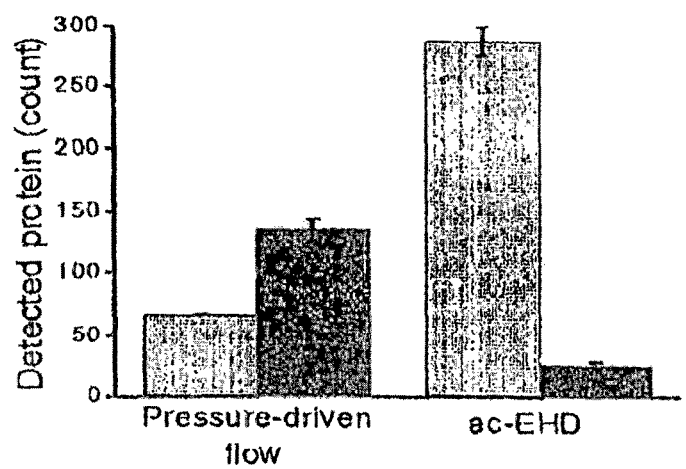
FIG. 30|ac-EHD induced nanoshearing effect on nonspecific adsorption of proteins. Fluorescence image analysis of the detected HER2 protein (gray) spiked in human serum along with mouse IgG (red) was run on EHD-μD3 under ac-EHD (f=1 kHz, V$_{pp}$=100 mV) and pressure-driven flow (control) conditions. Pressure driven flow based devices operated under the rate of 10 μLmin$^{-1}$ (an equivalent flow rate of that calculated based on the time required to flow 1 mL of serum sample under the given ac-EHD field). Each data point represents the average of three separate trials (n=3) and error bars represent standard error of measurements within each experiment.

To demonstrate the utility of the nanoshearing phenomena in removing nonspecific proteins present in serum samples, HER2 (500 pgmL$^{-1}$) along with nonspecific IgG (500 pgmL$^{-1}$) protein were spiked in serum and run on anti-HER2-functionalized devices. Under the ac field of f=1 kHz and $V_{pp}$=100 mV, the capture performance was evaluated using device EHD-µD3. An approximately 5-fold reduction (FIG. 30) in the number of nonspecific proteins that adhere to the electrode surface in comparison to the pressure-driven flow based device was observed. This data clearly demonstrates that nanoshearing phenomenon is highly effective in reducing nonspecific adsorption of proteins in comparison with pressure driven flow based approach.

Figure 31:
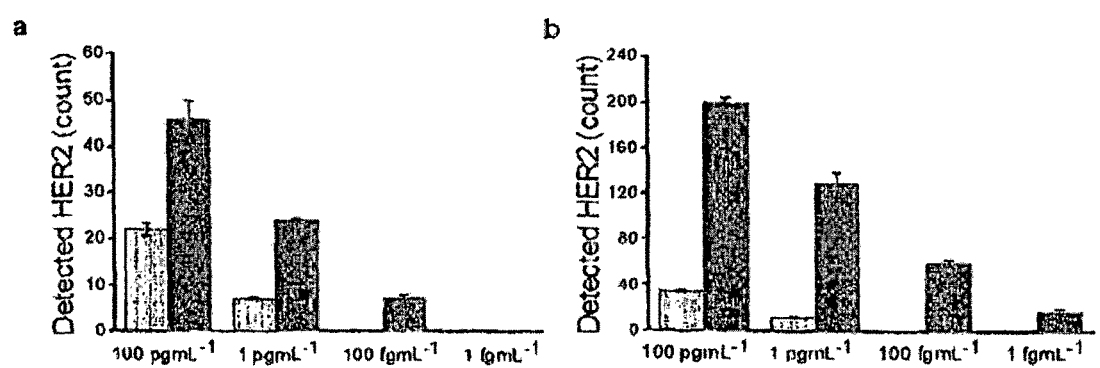
FIG. 31|ac-EHD induced nanoshearing for HER2 capture. (a,b) Fluorescence image analysis of the detected HER2 protein (100 pgmL$^{-1}$ to 1 fgmL$^{-1}$) spiked in human serum under ac-EHD (f=1 kHz, V$_{pp}$=100 mV; dark gray bar) and pressure driven flow (control; light gray bar) conditions in (a) EHD-μD1 and (b) EHD-μD3. Pressure driven flow based devices operated under the rate of 10 μLmin$^{-1}$ (an equivalent flow rate of that calculated based on the time required to flow 1 mL of serum sample under the given ac-EHD field). Each data point represents the average of three separate trials (n=3) and error bars represent standard error of measurements within each experiment.
Figure 32:
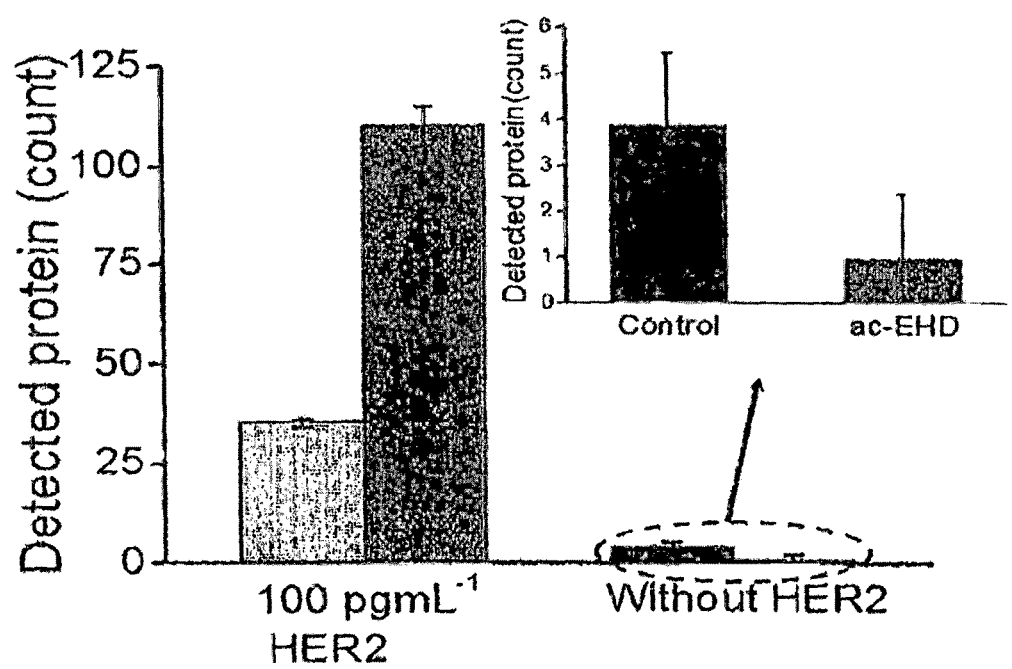
FIG. 32|Detection of proteins from human serum spiked with 100 pgmL$^{-1}$ (left bars in main panel) and without (right bars in main panel) HER2 under the ac-EHD field strength of f=1 kHz, V$_{pp}$=100 mV (dark gray and red bats) and pressure driven (control) flow conditions (light gray and blue bars). Pressure driven flow based devices operated under the rate of 10 μLmin$^{-1}$ (an equivalent flow rate of that calculated based on the time required to flow 1 mL of serum samples under the ac-EHD field strength of f=1 kHz, V$_{pp}$=100 mV). Each data point represents the average of three separate trials (n=3) and error bars represent standard error of measurements within each experiment.

To further assess the dynamic range and lower limit of detection (LOD) of the devices, designated concentrations of HER2 (100 pgmL$^{-1}$ to 1 fgmL$^{-1}$) were spiked in serum and run on anti-HER2-functionalized devices under the optimal ac field of f=1 kHz and $V_{pp}$=100 MV. Control experiments were performed with that of a pressure driven system to drive fluid through the devices at similar flow-rate. Under the ac-EHD field, fluorescence image analysis for Devices EHD-µD1 and EHD-µD3 suggested approximately 10 (FIG. 31($a$); 100 fgmL$^{-1}$ vs. 1 pgmL$^{-1}$ (control) for EHD-µD1) and 1000 fold (FIG. 31($b$); 1 fgmL$^{-1}$ vs. 1 pgmL$^{-1}$ (control) for EHD-µD3) increase in detection levels in comparison to the control devices. The linear dynamic range of detection for EHD-µD1 and EHD-µD3 was found to be 100 fgmL$^{-1}$-100 pgmL$^{-1}$ and 1 fgmL$^{-1}$-100 pgmL$^{-1}$, respectively. The enhanced HER2 capture with the use of ac-EHD induced fluid flow compared to the pressure driven flow based devices may be attributed to the synergistic effect of using a specific HER2 antibody, geometric arrangements of the antibody-functionalized microelectrode pairs within the channel, ac-EHD induced nanoshearing and concomitant fluid mixing phenomena. It is clearly noted that EHD-µD3 (FIG. 31($b$)) was sensitive enough to detect 1 fgmL$^{-1}$ HER2 antigen spiked in semi samples, while the minimum detectable concentration for EHD-µD1 was 100 fgmL$^{-1}$ (FIG. 31(a)). The LOD values obtained in scrum samples indicate that the method described herein can be used to detect low concentrations of molecular targets in complex fluids.

To further examine the effect of nanoshearing and concomitant fluid mixing to capture low concentration of target proteins in large excess of non-target proteins, two nonspecific proteins CA-125 (100 pgmL$^{-1}$) and PSA (100 pgmL$^{-1}$) were spiked in serum along with HER2 (1 fgmL$^{-1}$) and the effect was evaluated. EHD-µD3 was sensitive enough to detect 1 fgmL$^{-1}$ HER2 indicating that this device can detect low concentration of target proteins in the presence of a large excess of non-target proteins (10$^5$ fold higher concentration than target protein) in serum. This detection limit is comparable to that of the traditional bio-barcode, immuno-PCR, liposome-PCR, and redox-cycling based bioassays. Similar detection limits for serum protein detection have also been reported elsewhere using microfluidic based platforms. However, their practical application is restricted due to their complex detection procedures, complicated coupling chemistries, pre-concentration/modification steps and operational control systems. Furthermore, current methodologies for removing nonspecific adsorption of non-target serum proteins involves molecular coatings using complicated surface chemistry (e.g., self-assembled monolayers, polymer brushes, polymer based resins, etc) coupled with sophisticated detection techniques. In contrast, engendering fluid flow and also shearing off non-target proteins via alternating voltage on asymmetric electrodes-based microfluidic system could be a simple and powerful tool to reduce nonspecific adsorption of proteins and also enhance capture performance of the devices.

Additional protein capture experiments were performed by the inventors. The gold microelectrode pairs within the serpentine channel of an EHD-µD2 device were functionalized with an antibody specific to human epidermal growth factor receptor 2 (HER2) antigen. Designated concentrations of HER2 antigen was spiked in human serum and/or buffer samples and run through the device under the optimal ac-EHD conditions described above. The analytical performance of the ac-EHD device was compared with that of the pressure-driven flow (via a syringe pump) based devices. Captured HER2 proteins were detected using fluorescent tagged anti HER2 antibody under a fluorescence microscope.

Figure 33:
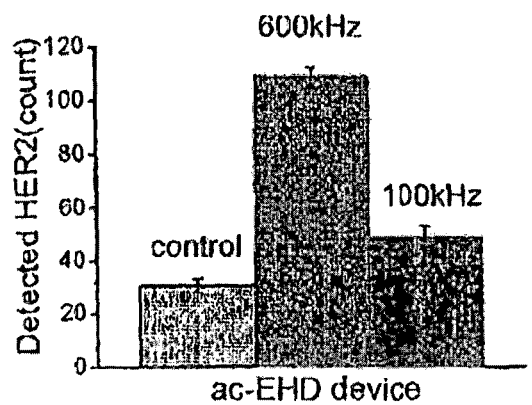
FIG. 33|HER2 protein capture at different ac field conditions. Fluorescence image analysis of HER2 (100 pgmL$^{-1}$ spiked in PBS) captured at the frequency of f=600 Hz (dark gray) and 100 kHz (red) at V$_{pp}$=100 mV in EHD-μD2. Control devices (light gray) include those tested under pressure driven flow conditions. Pressure driven flow based devices operated under the flow rate of 10 μLmin$^{-1}$ (an equivalent flow rate of that calculated based on the time required to flow 1 mL of sample under the given ac-EHD field). Each data point represents the average of three separate trials (n=3) and error bars represent standard error of measurements within each experiment.

To investigate the effect of nanoshearing on molecular target detection, HER2 antigen was spiked into PBS or human serum, and the capture performance of the device under an applied ac-EHD field was determined. Initially, the optimal ac-EHD field for effective target capture was determined by running spiked samples on anti-HER2 functionalized devices using the frequency (f) range of 600 Hz-100 kHz at a constant amplitude (V$_{pp}$) of 100 mV. FIG. 33 demonstrates typical fluorescence image analysis results for 100 pgmL$^{-1}$ HER2 antigen spiked in PBS at an applied EHD signal frequency of 600 Hz (central black column) and 100 kHz (right hand column) at V$_{pp}$=100 mV. The capture performance was found to decrease with increasing applied frequency, as evident from a 2 fold decrease in capture level for a frequency of 100 kHz in comparison to a low frequency of 600 Hz. The variation in capture with the applied field strength indicated that the stimulation of fluid flow around the capture domain at lower field strengths maximized the target capture.

The resulting decrease in capture level at higher field frequencies (e.g., f=100 kHz, V$_{pp}$=100 mV) is possibly due to stronger fluid flow that can limit effective protein-antibody collisions (a condition where shear forces>antibody-antigen affinity interaction). In contrast, at lower frequencies the effective protein-antibody interactions are higher due to the precise manipulation of shear forces within the double layer and the resulting fluid flow velocity under ac-EHD field. Therefore, low field strength (i.e., f=1 kHz, V$_{pp}$=100 mV) was used for further studies in investigating the role of nanoshearing in reducing nonspecific adsorption and detection of HER2 protein.

Figure 34:
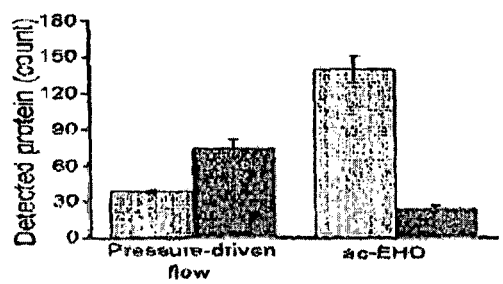
FIG. 34|ac-EHD induced nanoshearing effect on nonspecific adsorption of proteins. Fluorescence image analysis of the detected HER2 protein (gray) spiked in human serum along with mouse IgG (red) was run on EHD-μD2 under ac-EHD (f=1 kHz, V$_{pp}$=100 mV) and pressure-driven flow (control) conditions. Pressure driven flow based devices operated under the rate of 10 μLmin$^{-1}$ (an equivalent flow rate of that calculated based on the time required to flow 1 mL of serum sample under the given ac-EHD field). Each data point represents the average of three separate trials (n=3) and error bars represent standard error of measurements within each experiment.

The capture performance tinder ac-EHD flow was then compared to that of a hydrodynamic flow using a pressure-driven system (via a syringe pump) to drive fluid through the devices with the similar flow rate (10 µlmin$^{-1}$) observed under ac-EHD flow at f=1 kHz and V$_{pp}$=100 mV. Fluorescence image analysis data for the capture of 100 pgmL$^{-1}$ HER2 yielded a 4-fold increase in capture level under ac-EHD in comparison with pressure driven flow based controls. This high capture yield is presumably due to enhanced fluid mixing to facilitate effective antibody-antigen affinity interaction as a result of ac-EHD induced fluid flow. In another control experiment, the level of background response from the detection antibody using scrum samples spiked with (100 pgmL$^{-1}$) and without HER2 under similar ac-EHD (f=1 kHz, V$_{pp}$=100 mV) and pressure driven flow conditions was also tested, as shown in FIG. 34. However, negligible nonspecific binding of the detection antibody under the ac-EHD field was observed. This data suggests that ac-EHD induced nanoshearing can enflame the detection capabilities of the device and also possibly reduce nonspecific adsorption of non-target molecules.

Nonspecific adsorption of non-target proteins limits the capture performance of any detection system. The role of the nanoshearing phenomenon in reducing nonspecific adsorption of proteins using serum samples spiked with HER2 (500 pgmL$^{-1}$) along with nonspecific IgG (500 pgmL$^{-1}$) protein was investigated by running samples on anti-HER2 functionalized devices. Under the ac field of f=1 kHz and V$_{pp}$=100 mV, an approximately 3.5-fold reduction (FIG. 34) in the number of nonspecific proteins that adhere to the electrode surface was achieved in comparison to the pressure-driven flow based device. This data clearly demonstrates that nanoshearing phenomenon is highly effective in reducing nonspecific adsorption of proteins in comparison with pressure driven flow based approach.

Although this level of reduction in nonspecific adsorption is believed to be significant and relevant to clinical applications, further optimization of the ac-EHD procedure and device design may help to further reduce the nonspecific adsorption of molecules to specifically detect very low concentration of targets from complex samples.

Figure 35:
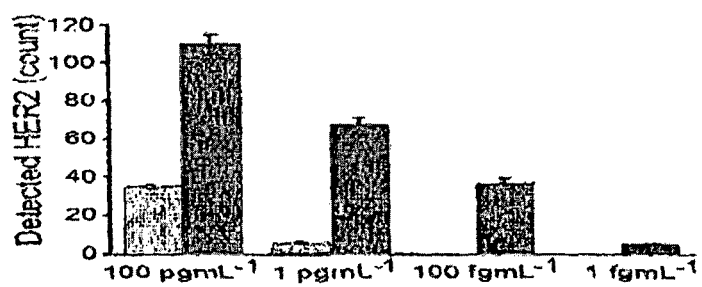
FIG. 35|ac-EHD induced nanoshearing for HER2 capture. Fluorescence image analysis of the detected HER2 protein (100 pgmL$^{-1}$ to 1 fgmL$^{-1}$) spiked in human serum under ac-EHD (f=1 kHz, V$_{pp}$=100 mV; dark gray bar) and pressure driven flow (control; light gray bar) conditions in EHD-μD2. Pressure driven flow based devices operated under the rate of 10 μLmin$^{-1}$ (an equivalent flow rate of that calculated based on the time required to flow 1 mL of serum sample under the given ac-EHD field). Each data point represents the average of three separate trials (n=3) and error bars represent standard error of measurements within each experiment.

To further assess the dynamic range and lower limit of detection (LOCI) of this device, designated concentrations of HER2 (100 pgmL$^{-1}$ to 1 fgmL$^{-1}$) wore spiked in serum and run on anti-HER2 functionalized devices under ac-EHD and conditions. Under the ac-EHD field, fluorescence image analysis suggested approximately a 1000 fold (FIG. 35; 1 fgmL$^{-1}$ vs. 1 pgmL$^{-1}$ (pressure driven flow)) increase in detection levels in comparison to the control devices. The resulting enhancement in HER2 capture with the use of ac-EHD induced fluid flow compared to the pressure driven flow based devices may be attributed to the synergistic effect of increasing electrode geometry (e.g., enhanced surface area), induced nanoshearing and concomitant fluid mixing. It is clearly noted that the device was sensitive enough to detect 1 fgmL$^{-1}$ HER2 antigen spiked in serum samples. This LOD value is 1000-fold lower than that reported previously in ac electro-osmosis and dielectrophoresis-based methods and is similar to the LOD values obtained in bioassays based on redox cycling, nanostructured electrodes, bio-bar code, carbon nanotube, and enzyme-amplified detections. This detection limit indicates that the method described herein can be used to detect low concentrations of molecular targets in complex fluids. Additionally, the unique capability to displace nonspecific molecules from electrode surface via tunable surface shear forces makes it a simple and effective approach ideally suited for protein detection from patient serum samples.

Finally, the effect of nanoshearing and concomitant fluid mixing to capture low concentration of target proteins in large excess of non-target proteins was investigated. Two nonspecific proteins CA-125 (100 pgmL$^{-1}$) and PSA (100 pgmL$^{-1}$) were spiked in serum along with HER2 (1 fgmL$^{-1}$), and the effect was evaluated under ac-EHD and pressure driven flow. It was evident that the device was sensitive enough to detect 1 fgmL$^{-1}$ HER2, even in the presence of large excess of non-target proteins ($10^5$ fold higher concentration than target protein) in serum.

Example IV—Colloid Rapture

A more detailed description al this example can be found in S. Rauf, M. J. A, Shiddiky, and M. Trau, *Colloidal Nanoshearing: Removal of non-specifically adsorbed biomolecular functionalized colloidal beads from surfaces*, ChemComm, Royal Society of Chemistry (2014), the entirety of which is hereby expressly incorporated herein by reference.

Colloidal micro and nanoparticles are ubiquitous owing to their diverse properties and numerous applications. Over the past few decades, biologically functionalized colloidal particles have received wide attention as transduction labels in bioassays for the detection of molecular and cellular targets such as DNA, proteins or cancer cells. Often, these assays are performed on solid surfaces that are functionalized with different affinity reagents (e.g., antibody biomolecules) and involve readouts such as fluorescence, surface enhanced Raman scattering or electrochemistry. Colloidal particles, however, tend to adsorb non-specifically to solid surfaces, e.g., on gold electrode surfaces, and thus can significantly affect the specificity and sensitivity of solid-phase biomolecular assays. Generically, the problem of selectively capturing colloids with specific surface chemistry versus colloids which bind to solid surfaces due only to non-specific physical forces (such as electrostatic or van der Waals colloidal forces) is also of potentially broad interest to the chemistry community.

Currently, several methods have been reported to reduce nonspecific adsorption of colloidal particles or molecules. While all these methods have a low non-specific adsorption, their practical application is restricted due to the longer analysis time, complicated chemistries, and multiple washing steps.

Figure 36:
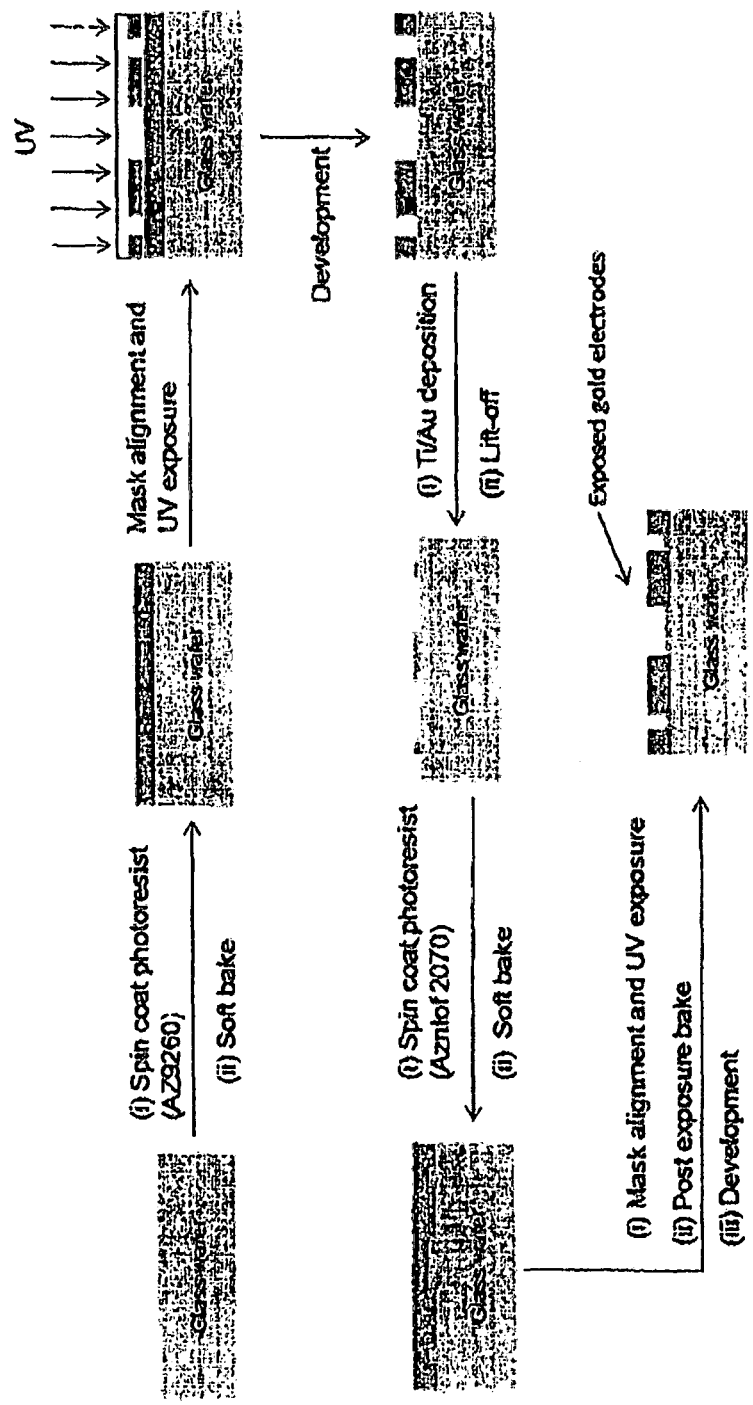
FIG. 36|Schematic representation of the fabrication of asymmetric electrodes pairs.

FIG. 36 shows the fabrication process of the devices used in these studies. Pyrex glass wafers (4", 1 mm thick, double-side polished) were obtained from Bonda technology, Singapore and sodalime chrome masks (5"×5") were obtained from Qingyi Precision Maskmaking (Shenzhen) Ltd, China. The microdevices were designed using Layout Editor (L-Edit V15, Tanner Research Inc., CA). Before photolithography, the glass wafers were cleaned by sonication in acetone and Isopropanol (IPA) and dried under flow of nitrogen gas. The devices were fabricated in two photolithography steps. In the first step, the cleaned glass wafers were coated with positive photoresist (AZ9260 Microchemicals, Germany) to obtain a ~7 μm thick resist layer (4000 rpm for 60 s), followed by a soft bake for 7 min at 110° C. The positive photoresist coated wafers were then UV exposed (1000 mJ/cm2) using a mask Wiper (EVG620, EV Group GmbH, Austria) and developed in AZ 726 developer solution (Microchemicals, Germany) for 8 min, followed by rinsing with deionized (DI) water (Millipore Pvt. Ltd., Australia) and dried under the flow of nitrogen gas. The wafers were then treated with oxygen plasma (60 watt for 45 s) to remove any residual resist layer in the developed patterns. The gold deposition (10 nm of titanium as adhesion layer followed by 200 nm of gold layer) was done using an e-beam evaporator (Temescal BJD-2000 E-beam). Finally, the asymmetric pair of gold electrodes were obtained via the acetone lift-off process.

Figure 37:
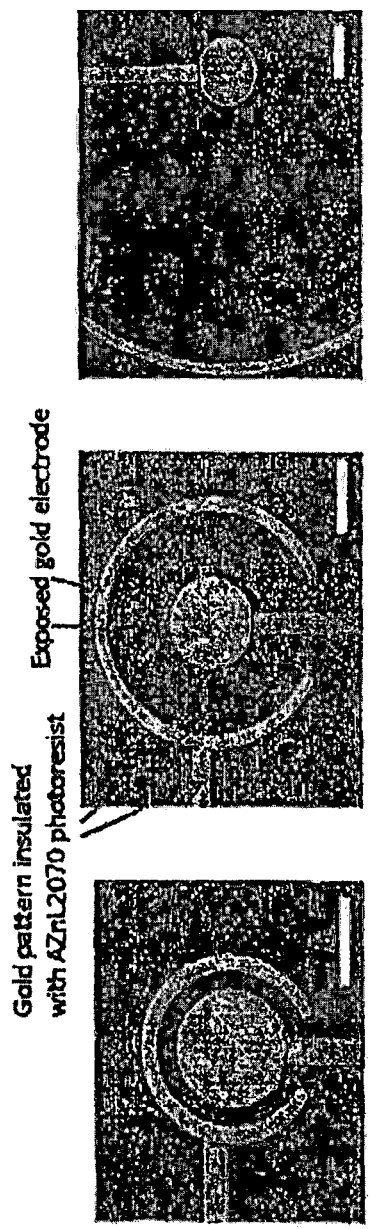
FIG. 37|Brightfield images of the fabricated electrodes (from left to right 50, 200 and 1000 μm edge to edge spacing between the electrode pairs). The diameter of the inner circular electrode is 250 µm. The width of the outer ring electrodes is 30 µm. The scale bar is 200 µm.

Images of the three resulting device types are shown in FIG. 37. In each device type, the inner circular electrode has the same diameter of 250 μm, and the width of the outer ring electrode was 30 μm. However, the size (e.g., geometric area) of the outer electrode is determined by the distance between the inner and outer electrode (edge to edge distance between inner and outer electrode=$d_{e-e}$) which is 50 μm, 200 μm and 1000 μm in respective devices types. These electrodes were connected with the ac signal generator via the large gold connecting pads of 7×2 nm2 and work as cathode or anode of an electrolytic cell during the ac-EHD experiments.

In the second lithography step, the gold electrodes were coated with a negative photoresist (AZnL2070, Microchemicals, Germany) at 3000 rpm for 30 s to obtain ~7 μm thick resist layer. After soft baking at 110° C. for 3 min, the wafers were exposed using the mask aligner and developed in AZ 726 developer solution to expose the gold electrodes and connecting pads. All other areas of the devices were covered with the resist layer (i.e., working area of the electrodes is only exposed to solution). The geometric area or working area of the inner circular electrode was $4.9 \times 10^4$ μm$^2$. The geometric areas of the outer electrodes with $d_{e-e}$=1000, 200 and 50 μm were found to be $2.1 \times 10^5$, $6.4 \times 10^4$ and $4.9 \times 10^4$ μm$^2$, respectively. The wafers were then diced into individual devices using a dicing machine (ADT-7100). Before using the devices, an oxygen plasma cleaning (100 watts, 45 s) was performed to remove any residual resist particles present on the electrode surface.

Real-time fluorescence measurements were performed using a Nikon eclipse fluorescence microscope equipped with a dual band pass filter set (ET-FITC/CY3) and a high speed colour CCD camera in order to observe green and red fluorescent beads simultaneously. A PDMS spacer of ~0.4 mm thick having 5 mm hole in the centre was placed on top of the electrode pair, which defines the volume of the working chamber. In each experiment, 15 μL of the solution was dropped on the electrode and covered with a glass coverslip to seal the chamber. The glass cover slip allowed viewing of the underlying electrodes with the microscope objective. The device was then connected to a signal generator (Agilent 33510B waveform Generator, Agilent Technologies, Inc., CA) via gold connecting pads and a BNC connector to apply ac electric field. Biotinylated gold electrodes were used to capture streptavidin coated beads. Briefly, the electrodes were initially incubated overnight at room temperature in 10 mM aqueous solution of cysteamine hydrochloride. After washing with plenty of de-ionized water electrodes were dry under a flow of nitrogen gas. These electrodes were then incubated ill 3 mg/mL solution of Mink sulfo-NHS-LC-biotin in 10 mM PBS pH 7.4 for 3 h. To remove any unbound EZLink sulfo-NHS-LC-biotin, these electrodes were washed three times with PBS solution.

In this study, the streptavidin coated dragon green fluorescent and carboxyl functionalized suncoast yellow fluorescent microspheres were used as specific and non-specific beads, respectively. Designated percentages of the specific and non-specific beads were used to make mixture solutions with designated amounts of green and red colour beads as shown in Table 1. The total number of beads per ml ($2 \times 10^9$) was kept constant for all the mixtures. The bead solutions were prepared in 1 mM PBS (i.e., 1 mM $NaH_2PO_4$, 1 mM $Na_2HPO_4$, and 13.7 mM NaCl). Only 15 μL of this mixture was dropped on the electrode surface. The ac field was applied wider different frequency (f) and amplitude ($V_{pp}$) and movement/attachment of the beads was observed in real time using a fluorescence microscope equipped with a high speed colour CCD camera.

TABLE 1

Percentage of different mixtures of beads used in the experiments.

| Formulation | Specific (%) | Non-specific (%) |
| --- | --- | --- |
| 1 | 0 | 100 |
| 2 | 25 | 75 |
| 3 | 50 | 50 |
| 4 | 75 | 25 |
| 5 | 100 | 0 |

Figure 38:
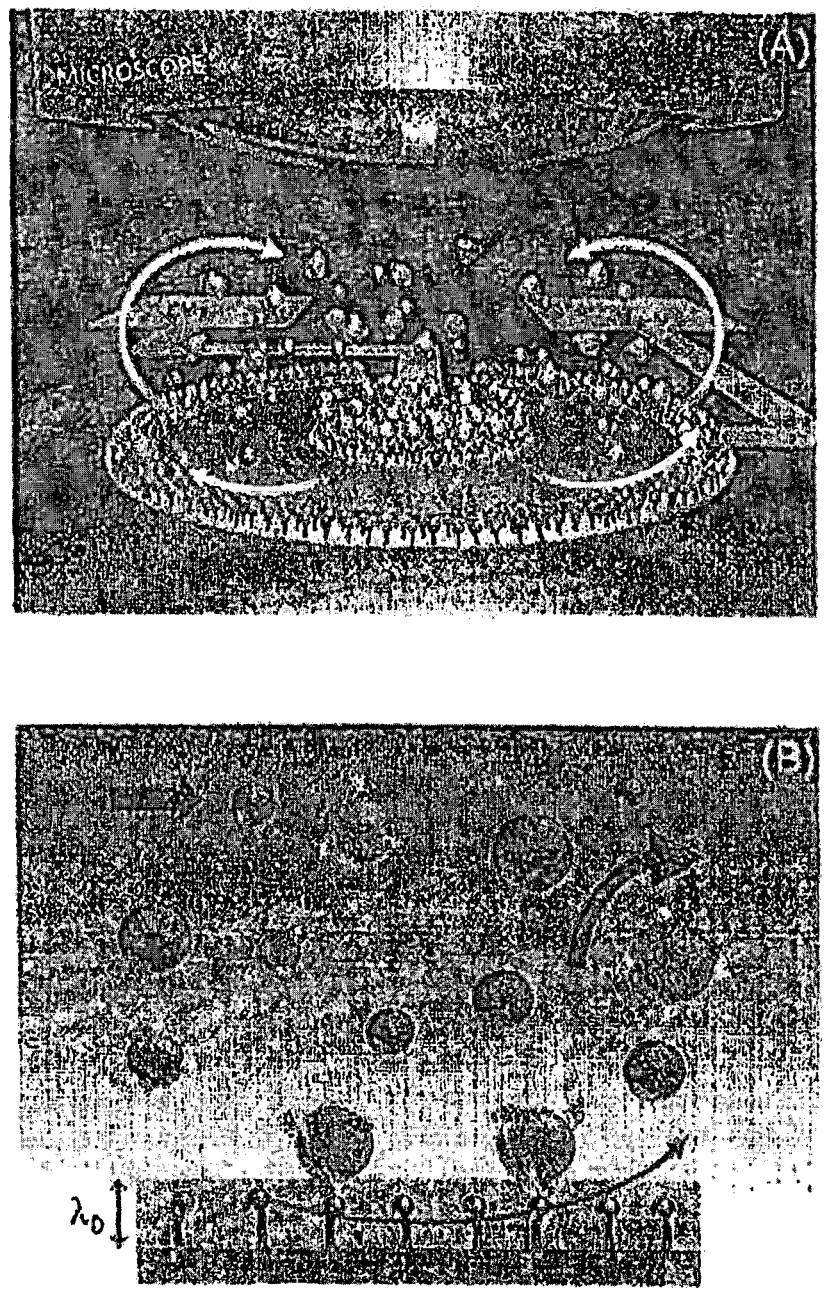
FIG. 38|(A) Schematic representation of the approach adopted for real-time visualization of the colloidal nanoshearing to enhance the capture efficiency of the colloids by increasing the number of sensor (functionalized surface)-target collisions, which is the result of the improved colloidal transport under ac-EHD fluid flow. (B) Schematic representation of capture of specific and removal of non-specific colloids via tuning the nanoscopic surface shear forces within the electrical double layer of the surface.

As can be seen in FIG. 38, large (ring type electrode) and small (inner circular electrode) electrodes in an asymmetric pair of the microelectrode form the cathode and anode (or vice versa) of an electrolytic cell. Devices with asymmetric electrode pairs were fabricated maintaining edge-to-edge distances between inner and outer electrode ($d_{e-e}$=50, 200 and 1000 μm). The diameter of the inner electrode and the width of the outer ring electrode were kept 250 and 30 μm respectively for all the devices. A 0.4 mm thick PDMS spacer with a 5 mm diameter hole was used to create the analysis chamber which was then filled with 15 μL of a mixture solution containing a designated amount of specific and nonspecific beads, and was then covered with a glass cover slip to complete the device.

Figure 39:
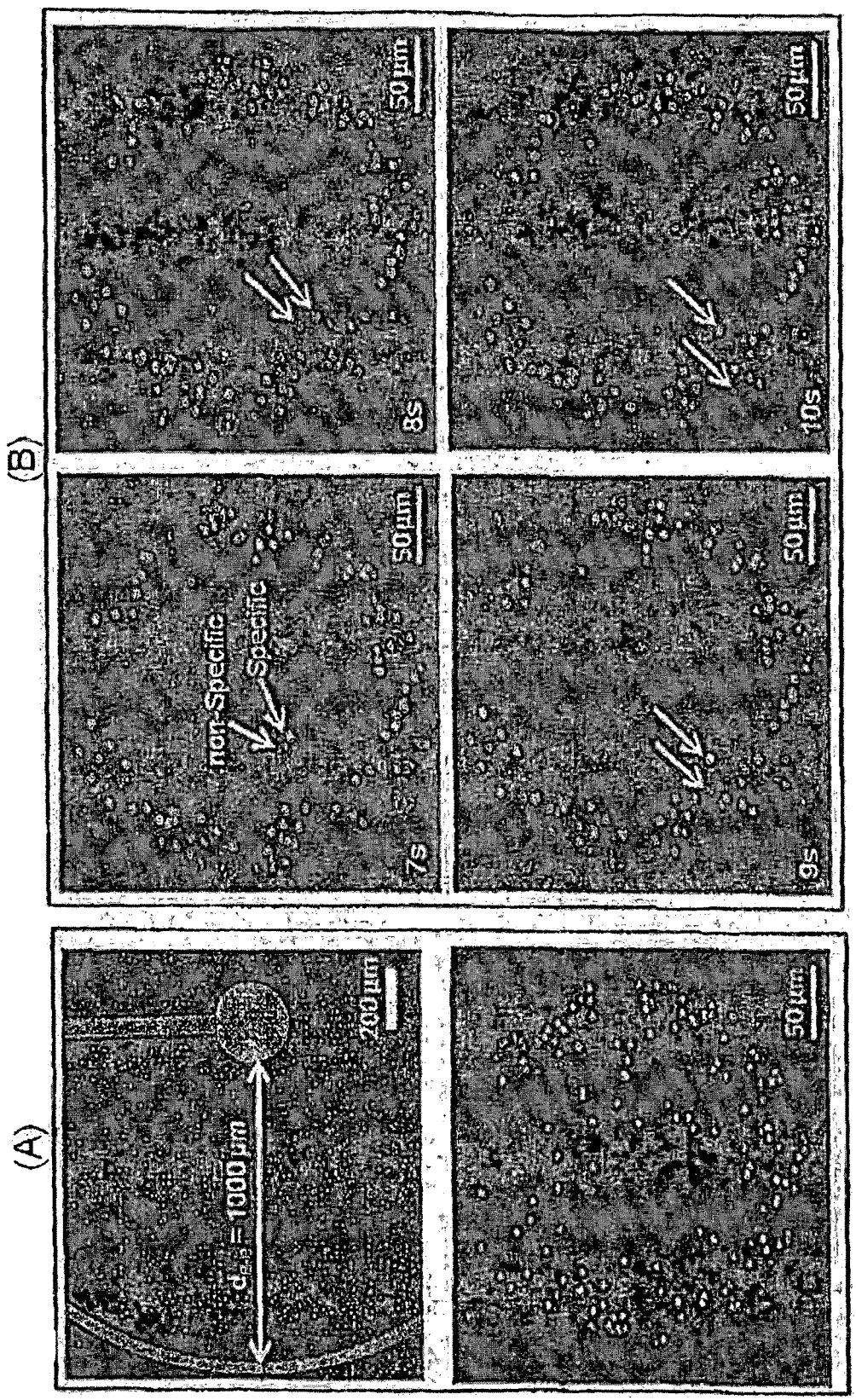
FIG. 39|(A) Brightfield microscopic image of an asymmetric electrode pair. The $d_{e-e}$ between middle and outer electrode is 1000 µm. The bottom fluorescence micrograph shows the capture of 50% specific beads in the presence of 50% nor-specific beads at the field strength of f=100 Hz and $V_{pp}$=4V. (B) Shows the snapshots from real time video showing the capture of streptavidin bead (green) and physical displacement of —COOH labelled bends (red) at the field strength of f=100 Hz and $V_{pp}$=4V. The green colour bead attached to the electrode and red colour bead was displaced from the electrode surface due to the surface shear forces.

FIG. 39(A) shows the brightfield image of the device containing an asymmetric pair of electrodes and fluorescence micrographs upon the capture of streptavidin labelled beads in presence of the nonspecific carboxyl beads under the ac-EHD field strength of frequency (f) 100 Hz and amplitude ($V_{pp}$) 4 V (inner electrode diameter 250 μm and de-e=1000 μm).

FIG. 39(B) shows the snapshots of real-time capture of specific beads and displacement of non-specific beads. The arrows in FIG. 39(B) are pointing the green and red coloured beads indicating the position of the beads on the electrode surface over the 4 s-period of nanoshearing induced capture process. These data clearly indicate that surface shear forces created by the ac field were strong enough to displace the non-specific carboxyl beads (red) while simultaneously enabled the enhanced capture of specific streptavidin beads (green) on the biotin-modified surface.

Figure 40:
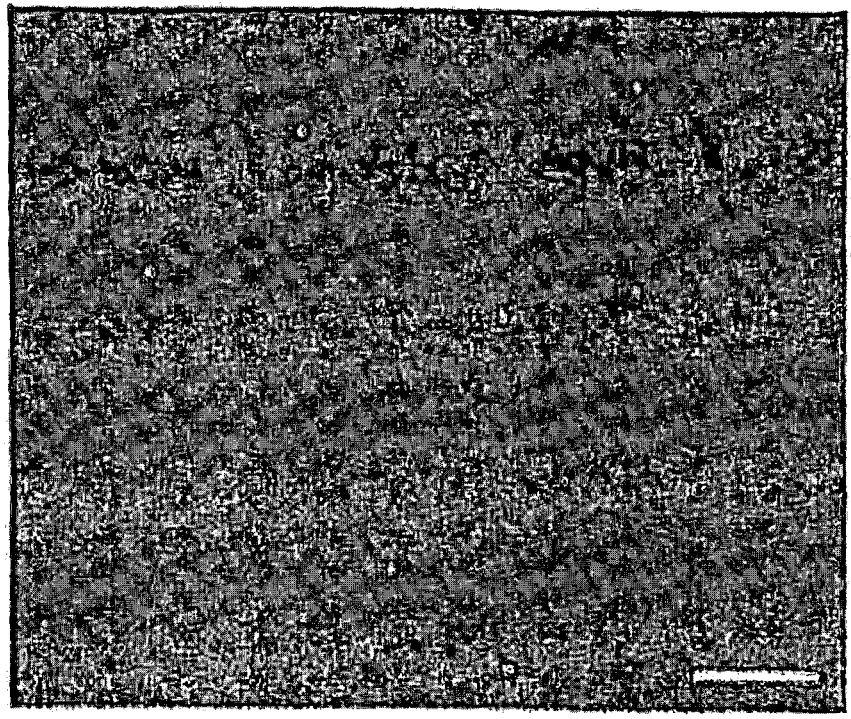
FIG. 40|Shows the comparison between biotin modified electrodes for specific capture of streptavidin beads with or without ac-EHD. The beads mixture was 50% specific and 50% non-specific. The incubation time in case of without ac-EHD was 24 h. The ac field strength of f=100 Hz and $V_{pp}$=4 V was applied for 5 min. The scale bar is 50 µm.
Figure 40:
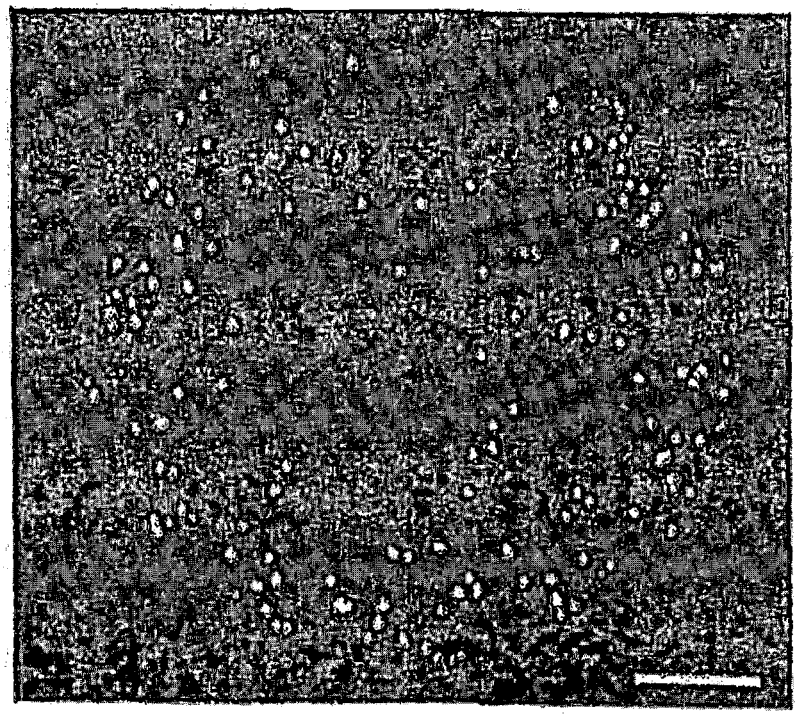

A control experiment was performed to check the capture performance of the devices without the use of ac-EHD field FIG. 40. A significantly low number of green and red beads were attached to the electrode surface after 24 hour incubation of devices in the mixture solution (i.e. 50% specific+ 50% non-specific). However, under the ac-EHD condition, the number of the captured specific beads was increased significantly due to the enhanced streptavidin-biotin collisions. In another control experiment, the capture performance of the ac-EHD method was checked using a device with bare gold electrodes FIG. 41. As expected, a relatively low number of specific and non-specific beads were observed at unmodified surface in comparison to the biotin-functionalized surface. Notably, the number of the specific beads at biotin-functionalized surface were significantly increased while the non-specific beads were almost similar in both cases. These data indicate that the surface shear forces created by the ac field can (i) selectively enhance the capture of streptavidin beads on biotin functionalized surface and (ii) effectively displace the non-specific species or beads from the electrode surface.

Figure 42:
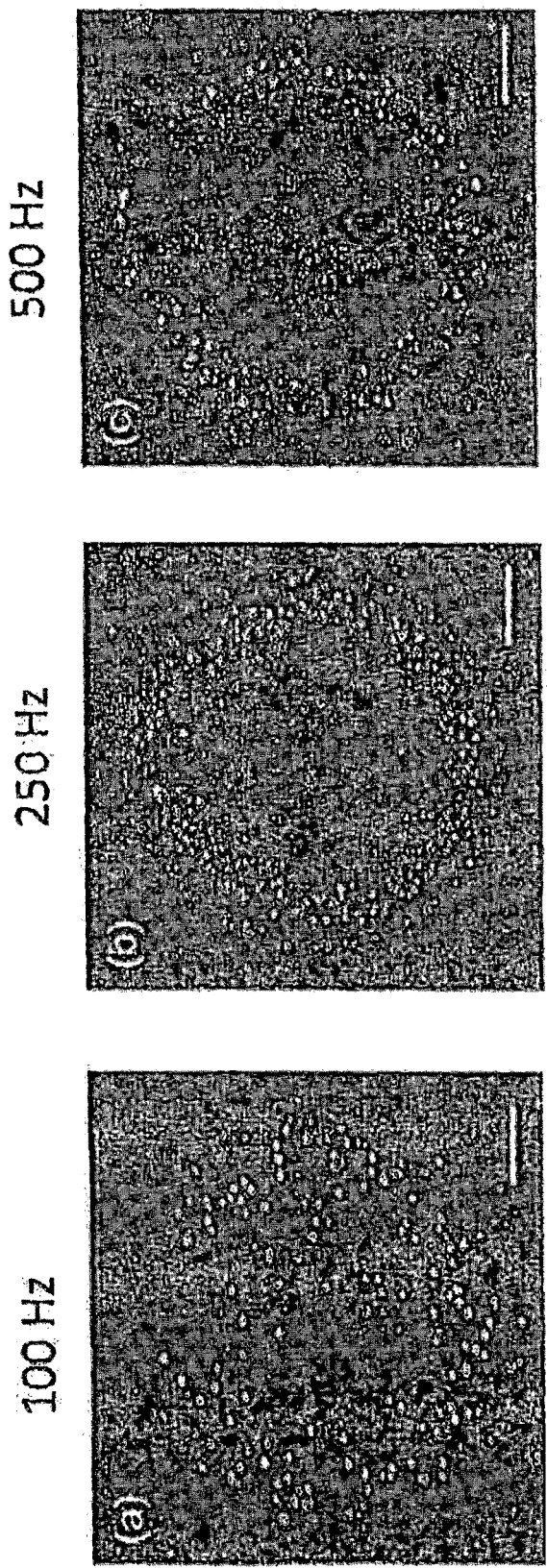
FIG. 42|Effect of the ac frequency on nanoshearing phenomenon. The snapshots of the middle electrode were taken from real-time videos after 5 min operation of the device under the frequency of (a) 100 Hz, (b) 250 Hz, and (c) 500 Hz at constant amplitude of 4 V. The scale her is 50 µm.
Figure 43:
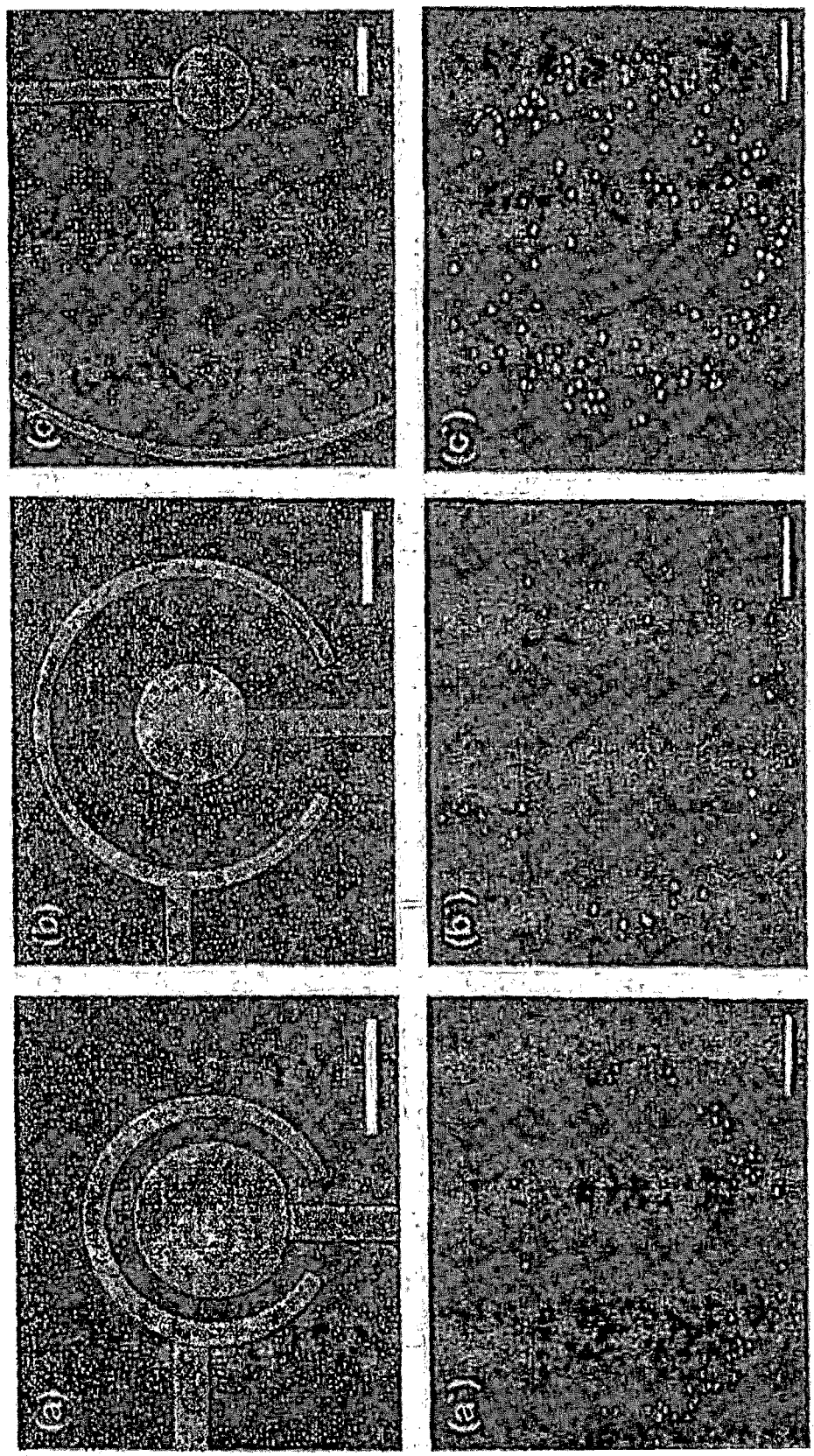
FIG. 43|Brightfield microscopic images of different asymmetric electrodes pairs with $d_{e-e}$ of (a) 50, (b) 200, and (c) 1000 µm. The diameter of the central electrode and thickness of the outer ring electrode in all cases is 250 and 30 µm, respectively. The scale bar is 200 µm. Corresponding (a', b' and c') capture efficiency for a mixture solution (50% specific and 50% non-specific) of beads under the field strength of f=100 Hz and $V_{pp}$=4 V. The scale bar is 50 µm.

The effect of different field strengths on the specific capture of streptavidin beads was evaluated by changing the frequency and amplitude of the applied ac field. It was found that at the field strength of f=100 Hz and $V_{pp}$=4 V, the shear forces were strong enough to displace the non-specific beads and capture maximum number of specific beads as compared to other frequencies FIG. 42. At frequencies higher than 100 Hz at $V_{pp}$=4 V, the shear forces become weaker and more number of non-specific beads were attached to the electrode surface. On the other hand, the field strengths resulted under f=100 Hz and $V_{pp}$=<4V, the beads moves slowly and take longer time to interact with the electrode surface (data not shown). However, at f=100 Hz and $V_{pp}$=5 V evolution of hydrogen gas due to electrolysis process damaged the electrodes within 2 mM of ac-EHD process (data not shown). Therefore, the field strength of f=100 Hz and $V_{pp}$=4 V was selected for all ac-EHD experiments.

Figure 41:
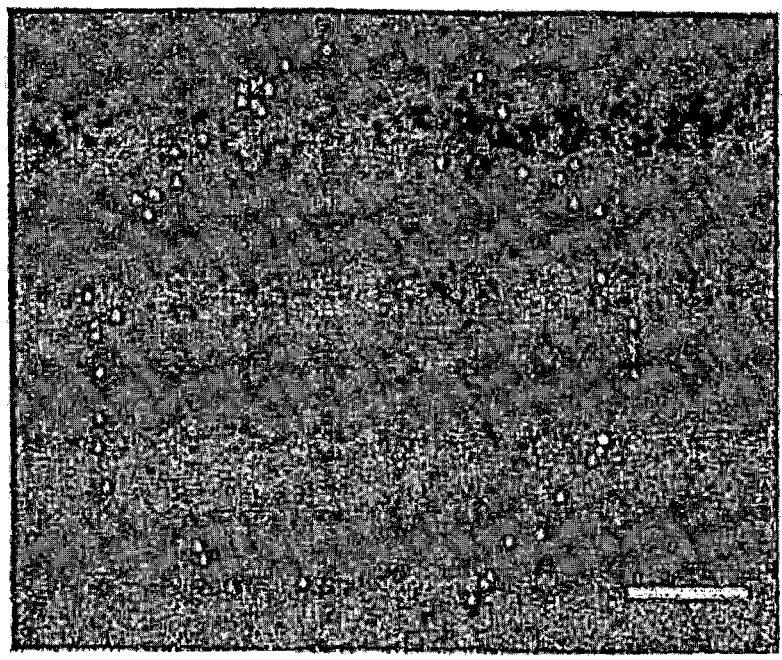
FIG. 41|Shows the comparisons between the unmodified (bare) and biotin modified electrodes for specific capture of streptavidin beads in the presence of —COOH modified beads (50% specific+50% non-specific). The ac field strength of f=100 Hz and $V_{pp}$=4 V. The scale bar is 50 µm.
Figure 41:
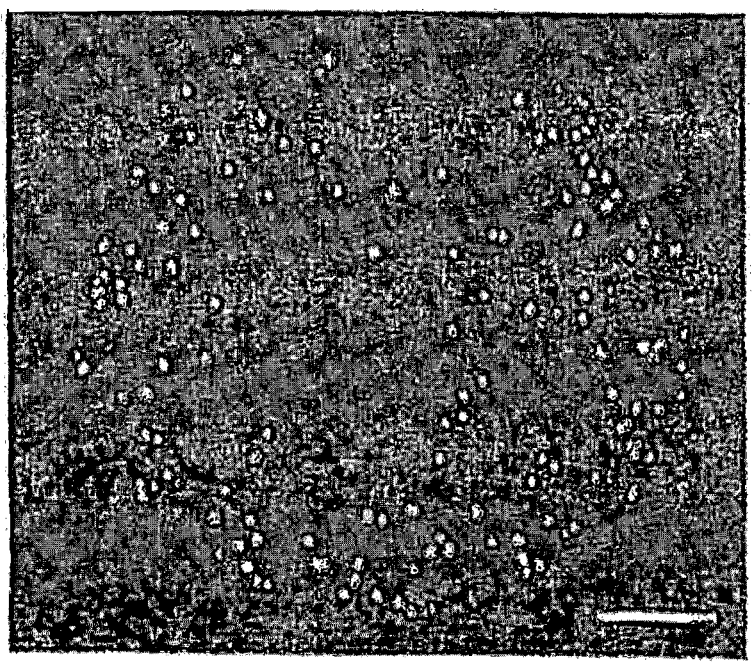
Figure 44:
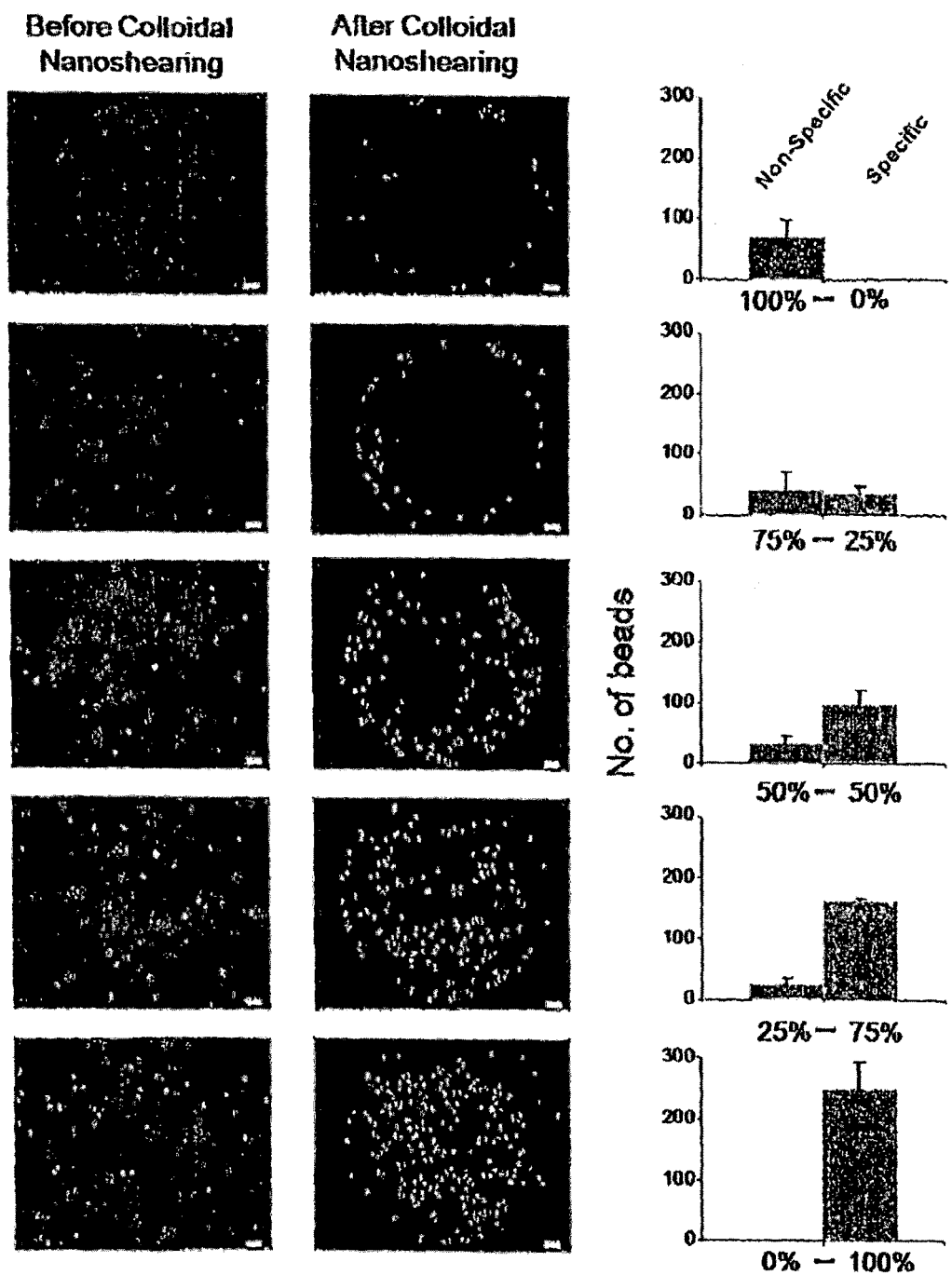
FIG. 44|Colloidal nanoshearing effect showing the decrease in non-specific adsorption and increase in the specific capture in the mixtures of streptavidin and —COOH labelled beads. The ac field strength parameters were f=100 Hz and $V_{pp}$=4 V. The central electrode diameter=250 µm and between middle and outer electrode is 1000 µm.

The performance of devices with different electrode designs was tested for the capture of specific beads in the presence of nonspecific beads under the optimal ac-EHD field. FIG. 41 shows the electrode with $d_{e-e}$ of 1000 μm captured maximum number of specific beads compared to the electrodes with $d_{e-e}$ of 200 and 50 μm. These data clearly indicate that the distance between the two electrodes has pronounced effect both on facilitating binding of specific species and enhancing removal of non-specific binding events. Since the asymmetric pair of electrodes with the $d_{e-e}$ of 1000 μm gives maximum effective collisions, it was selected for further experiments. In order to access the capture efficiency of the electrodes, five different mixtures of the specific and non-specific beads (100% non-specific, 75% non-specific+25% specific, 50% non-specific+50% specific, 25% non-specific+75% specific and 100% specific) were analyzed using the optimal experimental parameters (FIG. 44). In each mixture, the total number of the specific and non-specific beads were similar to that of either 100% specific or 100% non-specific beads (FIG. 44). The left panel in FIG. 44 shows the snapshots from the analysis chamber taken just before starting the ac-EHD induced capture and in-situ visualization processes. Clearly, the beads were floating in the PBS buffer under brownian motion. The middle panel showed the fluorescence micrographs obtained after performing ac-EHD induced capture process. To quantify accurate number of the captured (specific or non-specific) beads, the devices were washed three times with PBS before taking these images. The right panel in FIG. 44 shows the quantitative representation of the specific and non-specific beads attached on the electrode surface upon nanoshearing effect. It can be seen that capture efficiency of 100% specific beads is approximately three-fold higher compared to that of the 100% non-specific beads (a similar number of beads were used in both experiments). In case of 50/50% mixture of specific and non-specific beads, a similar level of enhancement in capture efficiency of specific beads was found. Capture efficiency of the 25% specific, beads in presence of the 75% non-specific beads was over 2-fold higher compare to that of the 25% non-specific in presence of the 75% specific one. These data clearly indicate that the nanoshearing effect is able to specifically capture target beads in the presence of the 3-fold higher non-specific beads.

The capture methods and devices described herein are able to capture target cells, molecules, and/or other target entities with high efficiency and specificity, including the detection of cancer cells in buffer or lysed blood. The use of ac-EHD to induce fluid flow in fluidic channels not only avoids the need for external pumping, but more importantly enables the microscale or nanoscale manipulation of fluid flows and shear forces ('nanoshearing') to enhance capture efficiency and reduce nonspecific adsorption. The devices are able to analyse large sample volumes (highly desirable for rare CTC isolation in clinical samples), and uses non-covalent binding of antibodies (avoids the need of using covalent coupling chemistries).

The analytical performances of the described devices and methods (87% capture efficiency for 100 cells mL$^{-1}$ in blood samples, with a 4-fold decrease in the non-specific adsorption of cells) indicate that ac-EHD devices as described herein will be useful for the quantification of low-abundance cells from complex mixtures with minimal sample pre-processing. These devices and methods are capable of stand-alone use or use in tandem with current technologies for CTCs detection. The potential to preserve cell viability could facilitate detailed molecular and functional characterization of rare cells, making the methods and devices potentially attractive for integration into clinical settings. In any case, the described devices and methods may constitute a new characterization and diagnostic tool for the early diagnosis of cancer metastasis and/or early detection of recurrence.

Many modifications will be apparent to those skilled in the art without departing from the scope of the present invention.

The invention claimed is:

1. A method for the detection of target entities, the method including:
   introducing a liquid sample containing at least one type of target entity to be detected into a fluidic channel;
   wherein mutually spaced electrodes are disposed along the fluidic channel and are functionalised to selectively bond to the at least one type of target entity, the mutually spaced electrodes being configured to electro-hydrodynamically pump the liquid sample along the fluidic channel on application of a signal to the electrodes;
   selecting one or more parameters of a signal to be applied to the electrodes to provide enhanced selectivity of the at least one type of target entity by selectively shearing non-specifically adsorbed cells and/or molecules from the electrodes; and
   applying a signal having the selected one or more parameters to the electrodes to electro-hydrodynamically pump the liquid sample along the fluidic channel and capture the at least one type of target entity at the functionalised electrodes, wherein:
   (i) the signal applied to the electrodes is a DC signal, the selectivity is determined by the voltage of the DC signal, and the step of selecting the one or more parameters includes selecting a voltage of the DC signal to provide enhanced selectivity of the at least one type of target entity; or
   (ii) the signal applied to the electrodes is an AC signal, the selectivity is determined by the amplitude and frequency of the AC signal, and the step of selecting the one or more parameters includes selecting at least the frequency of the AC signal to provide enhanced selectivity of the at least one type of target entity.

2. The method of claim 1, wherein the signal applied to the electrodes is an AC signal, and the selectivity has a maximum as a function of the frequency of the AC signal applied to the electrodes, and the step of selecting at least one of the one or more parameters includes selecting a frequency of the AC signal to provide enhanced selectivity of the at least one type of target entity.

3. The method of claim 2, including selecting at least one parameter of the AC signal other than frequency to further enhance the selectivity of the at least one type of target entity.

4. The method of claim 1, including selecting at least one parameter of the signal to selectively remove a selected entity from the electrodes.

5. The method of claim 1, including controlling at least one parameter of the signal to correspondingly control shear forces near the electrodes.

6. The method of claim 1, wherein the at least one type of target entity includes at least one type of biological entity.

7. The method of claim 6, wherein the at least one type of biological entity includes at least one type of cell, DNA, RNA, and/or protein biomarker.

8. The method of claim 6, wherein the at least one type of biological entity includes at least one type of circulating tumor cell.

9. The method of claim 1, wherein the selected at least one parameter of the signal increases the efficiency of capture of the at least one type of target entity.

* * * * *